(12) United States Patent
Creasy

(10) Patent No.: US 12,263,245 B2
(45) Date of Patent: Apr. 1, 2025

(54) IMMUNOMODULATING TREATMENTS OF BODY CAVITIES

(71) Applicant: UROGEN PHARMA LTD., Ra'anana (IL)

(72) Inventor: Caretha L. Creasy, Philadelphia, PA (US)

(73) Assignee: UROGEN PHARMA LTD., Ra'anana (IL)

( * ) Notice: Subject to any disclaimer, the term of this patent is extended or adjusted under 35 U.S.C. 154(b) by 0 days.

(21) Appl. No.: 18/665,612

(22) Filed: May 16, 2024

(65) Prior Publication Data

US 2024/0382420 A1 Nov. 21, 2024

Related U.S. Application Data

(60) Provisional application No. 63/502,418, filed on May 16, 2023.

(51) Int. Cl.
| | | |
|---|---|---|
| A61K 9/06 | (2006.01) | |
| A61K 31/403 | (2006.01) | |
| A61K 31/4738 | (2006.01) | |
| A61K 31/7072 | (2006.01) | |
| A61K 47/10 | (2017.01) | |
| A61P 35/00 | (2006.01) | |
| C07K 16/28 | (2006.01) | |
| A61K 39/00 | (2006.01) | |

(52) U.S. Cl.
CPC ............. *A61K 9/06* (2013.01); *A61K 31/403* (2013.01); *A61K 31/4738* (2013.01); *A61K 31/7072* (2013.01); *A61K 47/10* (2013.01); *A61P 35/00* (2018.01); *C07K 16/2818* (2013.01); *A61K 2039/505* (2013.01); *A61K 2039/545* (2013.01)

(58) Field of Classification Search
CPC .... A61K 9/06; A61K 31/403; A61K 31/7072; A61K 47/10; A61K 2039/505; A61P 35/00; C07K 16/2818
See application file for complete search history.

(56) References Cited

U.S. PATENT DOCUMENTS

| | | | |
|---|---|---|---|
| 10,758,482 B2* | 9/2020 | Hakim | ................. A61K 9/0034 |
| 2022/0118096 A1* | 4/2022 | Konorty | ................. A61K 31/07 |
| 2022/0202773 A1 | 6/2022 | Hionidi | |
| 2023/0107927 A1 | 4/2023 | Glick | |

FOREIGN PATENT DOCUMENTS

WO 2023038899 3/2023

OTHER PUBLICATIONS

Zhang et al., World J. Clin Oncol May 24, 2020;11(5):275-282. (Year: 2020).*

* cited by examiner

*Primary Examiner* — Robert S Cabral
(74) *Attorney, Agent, or Firm* — JMB Davis Ben-David

(57) ABSTRACT

Provided herein are compositions and methods for treating cancer of a body cavity, including urinary tract cancer, by way of a combination of at least one immunomodulatory agent, such as a CTLA-4 antibody or TLR agonist, and optionally one chemotherapeutic agent, wherein one or more of the therapeutic agents are embedded in, and slowly released from, a biocompatible hydrogel composition.

21 Claims, 1 Drawing Sheet

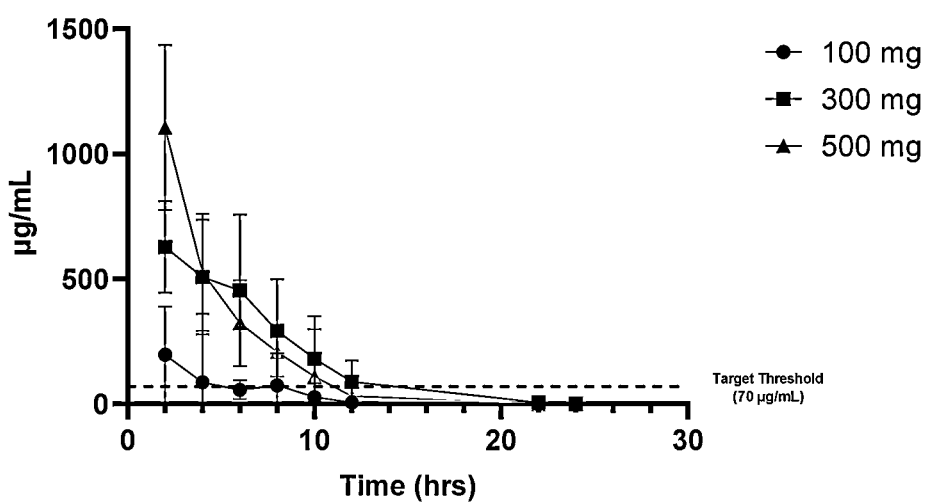

IMMUNOMODULATING TREATMENTS OF BODY CAVITIES

CROSS-REFERENCE TO RELATED APPLICATIONS

Benefit is claimed to U.S. Provisional Patent Application 63/502,418 filed May 16, 2023; the contents of which is incorporated by reference herein in its entirety.

FIELD

Provided herein are compositions and methods for treating cancer of a body cavity, including urinary tract cancer, by way of a combination of at least one immunomodulatory agent and optionally one chemotherapeutic agent, wherein one or more of the therapeutic agents are embedded in, and slowly released from, a biocompatible hydrogel composition either in combination or individually.

BACKGROUND

Cancers are diseases of uncontrolled proliferation of abnormal cells. Urothelial carcinoma of the urinary bladder represents more than 90% of all bladder cancers, about 80% of which are non-muscle invasive bladder cancer (NMIBC), a form of superficial cancer. Transurethral resection and radical cystectomy remain the mainstay of treatment for NMIBC and MIBC (muscle-invasive bladder cancer), respectively.

Standard treatment for high-grade (HG) NMIBC is transurethral resection of bladder tumors (TURBT) followed by adjuvant intravesical immunotherapy with *Bacillus* Calmette-Guerin (BCG). Approximately one-third of NMIBC patients will not respond to BCG, and among those who demonstrate an initial response, more than half will experience recurrence or progression during long-term follow-up. Radical cystectomy is strongly advocated in patients with BCG-unresponsive NMIBC (ie, patients with BCG-refractory and BCG-relapsing tumors in whom further BCG therapy is not recommended) due to the risk of invasive and metastatic disease, highlighting the need for nonsurgical treatment options in the setting of BCG failure.

Certain combinations of immunomodulating and chemotherapy compositions have been proposed to activate innate and/or adaptive immunity to target tumors. For example, anti-CTLA-4 antibodies have been investigated for use in treating various cancers, including bladder cancer. Evaluation of blood samples from patients treated systemically with two doses of ipilimumab (an anti-CTLA-4 antibody) showed increased expression of $CD4^+ICOS^{hi}$ T cells, which produced approximately five-fold increases in levels of IFN-γ compared to untreated patients suggesting that ipilimumab increases tumor-reactive cells. However, toxicity from systemic administration of certain treatments (e.g. anti-CTLA-4 antibodies) has limited their utility for such treatments.

Moreover, some immune response modulators have a relatively short half-life in terms of residence time within a given body cavity. It is known that such modulators appear to be cleared or metabolized, or simply diffuse away from a body cavity. This short residence duration may reduce the immune checkpoint modulator's ability to activate some immune system cells at the desired site.

Thus, there remains a substantial ongoing need for new means of controlling the delivery and the activity of immune checkpoint modulators in order to provide effective and safe treatments for bladder cancer.

SUMMARY

Described herein are pharmaceutical compositions, comprising an admixture of: (i) a thermoreversible hydrogel having a viscosity of not more than 5000 cP at 5° C., and a viscosity of $1\times10^6$ cP-$9\times10^7$ cP at 17° C.; and (ii) zalifrelimab liquid solution.

Additionally described herein are pharmaceutical compositions for use in treatment of bladder cancer, wherein the thermoreversible hydrogel is administered intravesically into a bladder of a subject thereby producing a voiding concentration of zalifrelimab of at least 20-70 μg/mL in urine of the subject after at least two hours of administration.

Also described herein is a kit for preparing the pharmaceutical composition comprising: (i) a thermoreversible hydrogel comprising 20%-32% of poloxamer 407, and (ii) a solution comprising 100 mg-750 mg of zalifrelimab, wherein mixing (i) and (ii) forms about 20-100 mL of the pharmaceutical composition.

An additional kit is described herein for preparing the pharmaceutical composition comprising: (i) 60-73 mL of a thermoreversible hydrogel comprising 20%-32% of poloxamer 407, and (ii) 2-15 mL of a solution comprising 100 mg-750 mg of zalifrelimab, wherein mixing (i) and (ii) forms about 75 mL of the pharmaceutical composition.

Also described herein is a kit for preparing the pharmaceutical composition comprising: (i) about 40-80 mL of a thermoreversible hydrogel (ii) about 1-10 mL of a mixture of a stabilizer, a reactive oxygen scavenger, a surfactant, a buffer, and a gelation temperature modifier, and (iii) about 10-20 mL of a solution comprising 50 mg-750 mg of zalifrelimab, wherein mixing (i) and (ii) and (iii) forms about 50-100 mL of the pharmaceutical composition.

Yet further described herein is a ready to use pharmaceutical composition to be administered to the patient, comprising Zalifrelimab, Poloxamer, a stabilizer, a buffer, a reactive oxygen scavenger and a gelation temp modifier.

Also described herein is a method for treating a urinary tract cancer, such as bladder cancer, comprising locally administering to a subject a pharmaceutical composition comprising an admixture of: (i) a thermoreversible hydrogel comprising 20%-32% (w/w) of poloxamer and water; and (ii) a solution comprising about 100 mg to about 700 mg zalifrelimab to the bladder of a patient in need thereof, wherein the pharmaceutical composition is formulated to provide sustained release of zalifrelimab over a period of about 2 to about 24 hours.

An additional method is described herein for treatment of a bladder cancer or regrowth of bladder cancer, comprising: intravesically administering to a subject a pharmaceutical composition comprising an admixture of: (i) a thermoreversible hydrogel comprising poloxamer and water; and (ii) a solution comprising about 100 mg to about 700 mg zalifrelimab, wherein the concentration of zalifrelimab in the pharmaceutical composition is 0.67-10 mg/mL; wherein the thermoreversible hydrogel has a viscosity of not more than 5000 cP at 5° C., and a viscosity of $1\times10^6$ cP-$9\times10^7$ cP at 17° C., and wherein the hydrogel produces a voiding concentration of zalifrelimab of at least 20-70 μg/mL in urine of the subject after at least 2 hours of administration, thereby treating the cancer.

Further described herein is a pharmaceutical composition, comprising: (i) a thermoreversible hydrogel comprising 20%-32% (w/w) of poloxamer and water; and (ii) about 30-100 mg/mL zalifrelimab formulated in a solution comprising 10-30 mM histidine, 200-300 mM sorbitol, 10-20 mM methionine, and 0.01-0.03% polysorbate 80, and is adjusted to a pH of 6-7.

Additionally described herein is a method for treatment of a bladder cancer comprising: (a) preparing a composition with an effective amount of Zalifrelimab solution into a thermoreversible hydrogel; and (b) administering the composition to the bladder wherein the thermoreversible hydrogel comprises: (i) 20% to 32% (w/w) poloxamer 407; (ii) 0.02% to 0.5% (w/w) hydroxypropylmethylcellulose; (iii) 0.5% to 1% (w/w) PEG-400; and (iv) water.

The foregoing and other objects, features, and advantages will become more apparent from the following detailed description, which proceeds with reference to the accompanying figures.

BRIEF DESCRIPTION OF THE FIGURES

FIG. 1 shows the mean (with a 95% confidence interval) UGN-301 urine concentrations versus nominal time, by treatment group and nominal time at concentrations of 100 mg, 300 mg, and 500 mg.

DETAILED DESCRIPTION

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids, polypeptides, and small molecules are approximate, and are provided for description. Although methods and materials similar or equivalent to those described herein can be used in the practice or testing of this disclosure, suitable methods and materials are described below. The term "comprises" means "includes." "Consisting essentially of" indicates a composition, method, or process that includes only those listed features as the active or essential elements, but can include non-active elements in addition. The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art, and as appropriate for the compound and the delivery system. For example, the compositions for use in the described methods are typically administered locally to the inside surface of a body cavity, such as by intravesical instillation (an exemplary form of local administration). An additional local administration route may be retrograde administration, such as to the upper urinary tract. Further examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Agonist: A molecule or compound that binds to a target and stimulates a biological response, similar to the biological response of the native substance that normally binds to the target. Targets can be receptors. Agonists are not limited to a specific type of compound, and may include in various embodiments peptides, and fragments thereof, and other organic or inorganic compounds (for example, peptidomimetics and small molecules). Agonists may be endogenous, exogenous, full, partial, inverse, irreversible, or selective.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure, and includes the "functional derivatives" described herein. A mimetic is a molecule that mimics the activity of another molecule, such as a biologically active molecule. Biologically active molecules can include chemical structures that mimic the biological activities of a compound. It is acknowledged that these terms may overlap in some circumstances. In particular embodiments of the claimed methods, analogs, derivatives, or mimetics having comparable activity to the expressly recited compounds can be used in place of the recited compounds.

Animal: Living multi-cellular vertebrate organisms, a category that includes for example, mammals and birds. The term mammal includes both human and non-human mammals. Similarly, the term subject includes both human and veterinary subjects, for example, humans, non-human primates, dogs, cats, horses, and cows. The term "primate" includes both human and non-human primates. "Non-human primates" are simian primates such as monkeys, chimpanzees, orangutans, baboons, and macaques. Similarly, the term "subject" includes both human and veterinary subjects, such as non-human primates, which have internal body cavities for which the described methods can be of benefit.

Antagonist: A molecule or compound that tends to nullify the action of another, or in some instances that blocks the ability of a given chemical to bind to its receptor or other interacting molecule, preventing a biological response. Antagonists are not limited to a specific type of compound, and may include in various embodiments peptides, antibodies and fragments thereof, and other organic or inorganic compounds (for example, peptidomimetics and small molecules). In a particular embodiment, an antagonist compound is one type of modulating compound.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce F (ab)$'_2$, a dimer of Fab which itself is a light chain joined to $V_H$-$C_H$ 1 by a disulfide bond. The F (ab)$'_2$ may be reduced under mild conditions to break the disulfide linkage in the hinge region thereby converting the F (ab)' 2 dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (Nature 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody (ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target— usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Body cavity: Any fluid-filled space internal to a multicellular organism. In particular embodiments, a body cavity can include other body cavities. For example, the mammalian pelvic cavity includes the bladder, and the thoracic cavity includes the upper gastro-intestinal tract and cavities such as the esophagus. In particular embodiments, a body cavity can be the urinary tract, such as the bladder and/or the pyelocaliceal system and/or the ureters.

Binding affinity: A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

Cancer: A malignant disease characterized by the abnormal growth and differentiation of cells. The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A "cancer cell" is a cell that is neoplastic, for example a cell or cell line isolated from a tumor.

Examples of solid tumors, such as sarcomas and carcinomas, and which include cancers of internal body cavities, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma and non-small cell lung carcinoma), ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Chemotherapeutic agent: An agent with therapeutic usefulness in the treatment of diseases characterized by abnormal cell growth or hyperplasia. Such diseases include cancer, autoimmune disease as well as diseases characterized by hyperplastic growth such as psoriasis. In one embodiment, a chemotherapeutic agent is a radioactive compound. One of skill in the art can readily identify a chemotherapeutic agent (for instance, see Slapak and Kufe, *Principles of Cancer Therapy*, Chapter 86 in *Harrison's Principles of Internal Medicine,* 14th edition; Perry et al., chemotherapy, Ch. 17 in Abeloff, *Clinical Oncology* 2$^{nd}$ ed., © 2000 Churchill Livingstone, Inc.; Baltzer L, Berkery R (eds): *Oncology Pocket Guide to chemotherapy,* 2nd ed. St. Louis, Mosby-Year Book, 1995; Fischer D S, Knobf M F, Durivage H J (eds): *The Cancer chemotherapy Handbook,* 4th ed. St. Louis, Mosby-Year Book, 1993). Chemotherapeutic agents include small molecule agents and biologic agents. The chemotherapeutic agent can be administered before, concurrently, or subsequent to the described methods for treatment of the cancer with the chemotherapy, immune checkpoint modulator and thermo-reversible hydrogel composition. An exemplary chemotherapy agent is gemcitabine, mitomycin C, oxaliplatin and docetaxel.

Contacting: Placement in direct physical association. Includes both in solid and liquid form. Contacting can occur in vitro with isolated cells or in vivo by administering to a subject. Exemplary form of contacting is via instillation.

Effective amount of a compound: A quantity of compound sufficient to achieve a desired effect in a subject being treated. An effective amount or "therapeutically effective amount" of a compound can be administered in a single dose, or in several doses, for example daily, during a course of treatment. However, the effective amount of the compound will be dependent on the compound applied, the subject being treated, the severity and type of the affliction, and the manner of administration of the compound. In a particular example, an effective amount of the active agents in the described compositions and treatments, namely the at least one chemotherapy and at least one immune check point modulator (i.e. inhibitor or inducing agent) is an amount that provides to a human subject receiving the composition, an anti-cancer effect that is greater than the effect that would be produced upon treatment with either agent alone, and which in particular embodiments is a synergistic effect.

Efficacy: Refers to the ability of agent to elicit a desired therapeutic effect. Efficacy also refers to the strength or effectiveness of a compound. As used herein, "enhancing efficacy" means to increase the therapeutic action of an agent. For example, when the agent is a chemotherapeutic agent, "enhancing efficacy" generally refers to increasing the ability of the agent to kill target cells, such as tumor cells.

Increased risk: As used herein "increased risk" of cancer refers to an increase in the statistical probability of developing cancer relative to the general population, or reoccurrence of cancer. For example, risk factors such as a prior history of bladder cancer can increase the risk of a subject experiencing reoccurrence of bladder cancer.

Intravesical instillation: Also known as "intravesical therapy;" a medical procedure involving the direct/local administration of a drug into the bladder. Comparable drug administration is possible for other body cavities. In particular embodiments, intravesical instillation involves delivery of a drug through a catheter. In particular embodiments of the methods described herein, hydrogel-based compositions, such as reverse thermal (thermoreversible) hydrogels are provided to a subject by intravesical instillation, either without or without prior mixing with an active agent, such as but not limited to zalifrelimab, imiquimod, or gemcitabine.

Inhibiting protein activity: To decrease, limit, or block an action, function or expression of a protein. The phrase inhibits protein activity is not intended to be an absolute term. Instead, the phrase is intended to convey a wide-range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Immunotherapy: A method of evoking an immune response against on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Pharmaceutically acceptable carriers: The active agents for use in the described methods can be, mixed with a pharmaceutically acceptable carrier. The pharmaceutically acceptable carriers useful in this disclosure are conventional. *Remington's Pharmaceutical Sciences*, by E. W. Martin, Mack Publishing Co., Easton, PA, 15th Edition (1975), and updates thereof, describes compositions and formulations suitable for pharmaceutical delivery of the compounds herein disclosed.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Pharmaceutically acceptable carriers: The pharmaceutically acceptable carriers useful in this disclosure are conventional. *Remington's Pharmaceutical Sciences*, by E. W. Martin, Mack Publishing Co., Easton, PA, 15th Edition (1975), and updates thereof, describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop. Preventing and treating a disease can also refer to the results of interventions taken to prevent the recurrence of a disease that has been otherwise treated, such as surgery to remove a solid tumor in an internal body cavity.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief. The radiotherapy can be administered before, concurrently, or subsequent to the described methods for treatment of the cancer with the chemotherapy, immune checkpoint modulator and thermoreversible hydrogel composition.

Subject susceptible to a disease or condition: A subject capable of, prone to, or predisposed to developing (or redeveloping) a disease or condition. It is understood that a subject already having or showing symptoms of a disease or condition is considered "susceptible" since they have already developed it.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Thermoreversible hydrogel: The thermoreversible hydrogels for use in the described compositions and methods are in liquid form at low temperatures and remain liquid in the process of administration to a patient (e.g. through intravesical instillation). At elevated temperatures (e.g. typical human body temperature), thermoreversible hydrogel solidifies, such as in a coating of an internal body cavity. Low temperature can be defined less than 20° C., preferably less than 15° C. In particular embodiment this low temperature can be less than 10° C. As used herein, a thermoreversible hydrogel is synonymous with a "reverse thermal hydrogel" and a "thermo-reversible hydrogel." Particular examples of a thermoreversible hydrogel include compositions such as RTgel, which include a poloxamer with additional optional ingredients.

Urinary tract cancer: Cancer of any area of the urinary tract, including the urothelium, kidney, renal pelvis ureter, bladder (also referred to as "urinary bladder"), lamina propria, bladder muscle and urethra. As defined by the T0, Ta, T1, T2, T3 and T4. Carcinoma in situ (CIS) is cancer found in the inner layer of the bladder lining. Surgery followed by intravesical instillation of chemotherapy is a common treatment for urinary tract solid tumors. Treatment with the described UGN-301, in combination with an additional therapeutic agent, such as a TLR agonist, and/or chemotherapeutic agent, may also be provided for treatment of cancer of the urinary tract as defined herein.

Wash: Use of a fluid to cleanse an area. In particular embodiments, the "wash" of an area results in complete cleansing of the area. In other embodiments, washing an area does not produce complete cleansing. In particular embodiments of the described methods, a body cavity is "washed" between application of compositions containing a hydrogel and a therapeutic agent. In particular embodiments, the composition is completely washed out of the body cavity. In other embodiments, the composition is not completely washed out of the body cavity. The wash (and removal of fluid) of the methods described herein can be accomplished by standard methods of introducing and removing fluid from a body cavity.

Overview of Several Embodiments

Described herein are pharmaceutical compositions, comprising an admixture of: (i) a thermoreversible hydrogel having a viscosity of not more than 5000 cP at 5° C., and a viscosity of $1 \times 10^6$ cP-$9 \times 10^7$ cP at 17° C.; and (ii) a zalifrelimab liquid solution.

In some embodiments, the pharmaceutical compositions comprising a thermoreversible hydrogel, comprises a poloxamer, particularly 25%-32% poloxamer.

In some embodiments, the pharmaceutical compositions comprising a thermoreversible hydrogel, comprise a thickener.

In yet further embodiments, the pharmaceutical compositions comprising a thermoreversible hydrogel comprises 20%-32% (w/w) poloxamer and a thickener is HPMC.

In some embodiments, the pharmaceutical compositions comprising a thermoreversible hydrogel comprises 25%-32% poloxamer, 0.02%-0.5% HPMC, 0.75%-1% PEG and water.

In some embodiments, the pharmaceutical compositions comprise a zalifrelimab liquid solution formulated in a solution comprising histidine, sorbitol, methionine, and polysorbate 80, and is adjusted to a pH of 6-7.

In some embodiments, the pharmaceutical compositions comprise a zalifrelimab liquid solution formulated in a solution comprising 10-30 mM histidine, 200-300 mM sorbitol, 10-20 mM methionine, and 0.01-0.03% polysorbate 80, and is adjusted to a pH of 6-7.

In some embodiments, the pharmaceutical compositions comprise zalifrelimab in a dose of 100 mg-750 mg.

In some embodiments, the pharmaceutical compositions comprise zalifrelimab with a concentration of 0.67-10 mg/mL.

In yet a further embodiment, the pharmaceutical compositions are formulated for intravesical administration into a bladder, and wherein at least about 80% of the detectable zalifrelimab is released from the thermoreversible hydrogel within about 2 to about 12 hours.

In other embodiments, the pharmaceutical compositions further comprises at least one additional therapeutic agent, in particular mitomycin C, imiquimod or gemcitabine.

In some embodiments, the pharmaceutical compositions provide a concentration of imiquimod from about 1 mg/mL to about 10 mg/mL.

In some embodiments, the pharmaceutical compositions provide a dose of gemcitabine from about 100 mg-3000 mg, in particular, up to about 2000 mg.

In some embodiments, the pharmaceutical compositions have a concentration of mitomycin C from about 0.1 mg/mL to about 4 mg/mL.

In some embodiments, the pharmaceutical compositions after a single intravesical administration the zalifrelimab urine concentrations exceeds 20 µg/mL.

In some embodiments, the pharmaceutical composition is substantially free from zalifrelimab aggregates after 24 hours, when stored at about 2° C.-8° C. for at least 24 hours.

In other embodiments, the thermoreversible hydrogel further comprises at least a stabilizer, a reactive oxygen scavenger, a surfactant, a buffer, and a gelation temperature modifier.

In some embodiments, thermoreversible hydrogel has a gelation temperature of about 10° C. to about 20° C., in particular 13° C. to about 16° C.

In other embodiments, the poloxamer is poloxamer 407.

In particular embodiments, the pH of the composition is from about 6 to about 8.

Further described herein are pharmaceutical compositions for use in treatment of bladder cancer, wherein the thermoreversible hydrogel is administered intravesically into a bladder of a subject thereby producing a voiding concentration of zalifrelimab of at least 20-70 µg/mL in urine of the subject after at least two hours of administration.

Additionally described herein is a kit for preparing the pharmaceutical composition comprising: (i) a thermoreversible hydrogel comprising 20%-32% of poloxamer 407, (ii) a solution comprising 100 mg-750 mg of zalifrelimab, wherein mixing (i) and (ii) forms about 20-100 mL of the pharmaceutical composition.

Also described herein is a kit for preparing the pharmaceutical composition comprising: (i) 60-73 mL of a thermoreversible hydrogel comprising 20%-32% of poloxamer 407, (ii) 2-15 mL of a solution comprising 100 mg-750 mg of zalifrelimab, wherein mixing (i) and (ii) forms about 75 mL of the pharmaceutical composition.

Additionally described herein is a kit for preparing the pharmaceutical composition comprising: (i) about 40-80 mL of a thermoreversible hydrogel, (ii) about 1-10 mL of a mixture of a stabilizer, a reactive oxygen scavenger, a surfactant, a buffer, and a gelation temperature modifier, and (iii) about 10-20 mL of a solution comprising 50 mg-750 mg of zalifrelimab, wherein mixing (i) and (ii) and (iii) forms about 50-100 mL of the pharmaceutical composition.

Also described herein is a ready to use pharmaceutical composition to be administered to the patient, comprising Zalifrelimab, Poloxamer, a stabilizer, a buffer, a reactive oxygen scavenger and a gelation temp modifier.

In some embodiments, the pharmaceutical composition contains a thermoreversible hydrogel comprising 25%-32% poloxamer, 0.02%-0.5% HPMC, and water.

In particular embodiments, the bladder cancer is high-grade or low grade NMIBC, MIBC, or carcinoma in situ (CIS).

Also described herein is a method for treating a urinary tract cancer, comprising locally administering to a subject a pharmaceutical composition comprising an admixture of: (i) a thermoreversible hydrogel comprising 20%-32% (w/w) of poloxamer and water; and (ii) about 100 mg to about 700 mg zalifrelimab to the bladder of a patient in need thereof, wherein the pharmaceutical composition is formulated to provide sustained release of zalifrelimab over a period of about 2 to about 24 hours.

In some embodiments, the thermoreversible hydrogel and zalifrelimab are mixed prior to administration of the composition.

In other embodiments, the method includes administering to the subject at least one additional therapeutic agent, in particular imiquimod, mitomycin C, gemcitabine or any combination thereof.

In some embodiments, the zalifrelimab and the additional therapeutic agent are administered separately, with an optional wash between the administration of the two agents.

In a particular embodiment, the pharmaceutical composition administered produces a zalifrelimab urine void concentration of at least 20 µg/mL after at least 2 hours of administration.

In some embodiments, the pharmaceutical composition is administered to the patient at least 6 times at about one-week intervals.

In some embodiments, the method includes administering the pharmaceutical composition at least once quarterly from month 6 from the first administration until month 12 from the first administration of the pharmaceutical composition.

In some embodiments, the bladder cancer is of high-grade or low grade NMIBC, MIBC, or carcinoma in situ (CIS).

In other embodiments, the composition is administered prior to surgical removal of a tumor or after removal of a tumor.

Additionally described herein is a method for treatment of a bladder cancer or regrowth of bladder cancer, comprising: intravesically administering to a subject a pharmaceutical composition comprising an admixture of: (i) a thermoreversible hydrogel comprising poloxamer and water; and (ii) about 100 mg to about 700 mg zalifrelimab, wherein the concentration of zalifrelimab in the pharmaceutical composition is 0.67-10 mg/mL; wherein the thermoreversible hydrogel has a viscosity of not more than 5000 cP at 5° C., and a viscosity of $1\times10^6$ cP-$9\times10^7$ cP at 17° C., and wherein the hydrogel produces a voiding concentration of zalifrelimab of at least 20-70 µg/mL in urine of the subject after at least 2 hours of administration, thereby treating the cancer.

In some embodiments, the method further includes administering to the subject an additional therapeutic agent selected from imiquimod, mitomycin C or gemcitabine. In particular embodiments, the additional therapeutic agent is administered prior to, concurrently with, or following administration of the pharmaceutical composition.

In particular embodiments, the pharmaceutical composition is administered once weekly for 3-9 weeks.

Additionally described herein is a pharmaceutical composition, comprising: (i) a thermoreversible hydrogel comprising 20%-32% (w/w) of poloxamer and water; and (ii) about 30-100 mg/mL zalifrelimab formulated in a solution comprising 10-30 mM histidine, 200-300 mM sorbitol, 10-20 mM methionine, and 0.01-0.03% polysorbate 80, and is adjusted to a pH of 6-7.

In some embodiments wherein the thermoreversible hydrogel comprises 25%-32% (w/w) poloxamer, and the zalifrelimab solution comprises about 50 mg/mL zalifrelimab, 20 mM histidine, 250 mM sorbitol, 15 mM methionine, and 0.02% polysorbate 80.

In other embodiments, the final concentration of zalifrelimab in the pharmaceutical composition is 0.67-10 mg/mL; and wherein the said pharmaceutical composition has a viscosity of not more than 5000 cP at 5° C., and a viscosity of $1 \times 10^6$ cP-$9 \times 10^7$ cP at 17° C.

Also described herein is a method for treatment of a bladder cancer comprising: (a) preparing a composition with an effective amount of Zalifrelimab solution into a thermorversible hydrogel; and (b) administering the composition to the bladder wherein the thermoreversible hydrogel comprises: (i) 20% to 32% (w/w) poloxamer 407; (ii) 0.02% to 0.5% (w/w) hydroxypropylmethylcellulose; (iii) 0.5% to 1% (w/w) PEG-400; and (iv) water.

In some embodiments, the composition comprises 24.8% poloxamer.

In other embodiments, the zalifrelimab has a concentration of 0.67-10 mg/mL.

In particular embodiments, the method includes intravesically administering to the subject an additional therapeutic agent selected from imiquimod, mitomycin C or gemcitabine.

Thermoreversible Hydrogels and Properties Thereof

Described herein are pharmaceutical compositions for sustained local delivery comprising a mixture of immuno-modulating antibodies and the thermoreversible hydrogel to be administered to a body cavity for treatment of cancer, such as bladder cancer. The pharmaceutical compositions of the present disclosure are thermoreversible hydrogels that are in certain embodiments mixed with stable solutions of an active agent prior to administration to a patient. Such hydrogels have relatively low viscosity at low temperatures, but at higher temperatures (e.g., body temperature) form a semi-solid gel which can serve as a drug depot in a body cavity such as the bladder, providing sustained release of active agents, such as zalifrelimab, over a period of about 3 to about 24 hours, including 3 hours, 4 hours, about 5 hours, about 6 hours, about 7 hours, about 8 hours, about 9 hours, about 10 hours, about 11 hours, or about 12 or about 14, or about 16 or about 18 or about 20 or about 24 hours, including all ranges between any of these values. The sustained release of the active agent, such as of zalifrelimab, provided by the compositions of the present disclosure provides improved efficacy, and improved tolerability compared to other types of compositions and modes of administration, such as systemic administration. Over time, the semi-solid gel formed after administration of the compositions of the present disclosure into a patient's body cavity slowly disintegrates, and when administered intravesically to the bladder, is excreted by normal urine flow.

The thermoreversible hydrogels of instant invention comprising at least one type (grade) of Poloxamer. Poloxamers are nonionic triblock copolymers comprising a central relatively hydrophobic chain of polypropylene oxide (PO) flanked by two relatively hydrophilic polyethylene oxide (EO) chains. The PO and EO chains can be of varying lengths and can be described by the average number of polypropylene oxide monomer units and ethylene oxide monomer units. Varying grades of poloxamer are suitable for use in the thermoreversible hydrogel compositions of the present disclosure, for example those described in U.S. Pat. Nos. 9,040,074 and 9,950,069, each of which is herein incorporated by reference in its entirety for all purposes. Suitable poloxamers include those manufactured by BASF under the trademark KOLLIPHOR and include for example KOLLIPHOR 407.

In particular embodiments, the thermoreversible hydrogel of the present disclosure comprise a poloxamer, such as Poloxamer 407, in amount of about 20 wt. % to about 32 wt. %, including about 22 wt. %, about 24 wt. %, about 25%, about 28 wt. %, about 29 wt. %, about 30 wt. %, or about 31 wt. % or about 32% including any ranges between any of these values of KOLLIPHOR 407 (or similar poloxamers having substantially the same composition). Further examples of the claimed thermoreversible hydrogel are described in U.S. Pat. No. 10,758,482, incorporated by reference in its entirety herein.

The compositions of the present disclosure can also be characterized by their thermally dependent properties (e.g., temperature-dependent viscosity and/or gelation temperature). The compositions of the present disclosure have a viscosity of not more than about 1000 cP at 5° C. (e.g., less than about 100 cP, about 100 cP, about 200 cP, about 300 cP, about 400 cP, and ranges of viscosities between any of about 100 cP, about 200 cP, about 300 cP, or about 400 cP or about 500 cP, or about 600 cP, about 700 cP, about 800 cP, about 1000 cP all measured at 5° C.). The compositions of the present disclosure have a viscosity ranging from about $1 \times 10^6$ cP to about $1.5 \times 10^7$ cP at 19° C., including about $2 \times 10^6$ cP, about $5 \times 10^6$ cP, about $6 \times 10^6$ cP, about $7 \times 10^6$ cP, about $8 \times 10^6$ cP, about $9 \times 10^6$ cP, about $1.0 \times 10^7$ cP, about $1.1 \times 10^7$ cP, about $1.2 \times 10^7$ cP, about $1.3 \times 10^7$ cP, about $1.4 \times 10^7$ cP, or about $1.5 \times 10^7$ cP, including all ranges between any of these values (all measured at between 17-21° C., in particular, 19° C.).

Viscosities as described herein are measured using viscometers common in the field, such as but not limited to a Brookfield viscometer.

The gelation temperature of the hydrogel of the present disclosure defines the temperature at which the compositions of the present disclosure exhibit a sharp increase in viscosity. The thermoreversible hydrogel of the present disclosure have a gelation temperature ranging from about 10° C. to about 20° C., including about 10° C., about 11° C., about 12° C., about 13° C., about 14° C., about 15° C., about 16° C., about 17° C., about 18° C., about 19° C., about 20° C. including all ranges between any of these values. In particular embodiments, the gelation temperature ranges from about 11° C. to about 20° C., or about 12° C. to about 14° C.

In the specific embodiment the pharmaceutical composition of the present disclosure comprise Zalifrelimab and one or more of a stabilizer, a reactive oxygen scavenger, a surfactant, a buffer, a thermoreversible hydrogel, gelation temperature modifiers and a thickener.

In particular embodiments thickeners include modified celluloses such as hydroxypropyl methylcellulose, methylcellulose, hydroxypropyl cellulose, carboxy-methylcelluloses and salts thereof, ethylcellulose; synthetic polymers such as polyacrylic acids and polymethacrylates; gelatin; starch and starch derivatives; gums such as guar gum and xanthan gum; and combinations of any of the preceding thickeners. In particular embodiments, the compositions of the present disclosure comprise hydroxypropyl methylcellulose (HPMC).

Suitable stabilizers for the compositions of the present disclosure include sugars or sugar alcohols, including sucrose, lactose, glucose, fructose, maltose, mannitol, sorbitol, xylitol, lactitol, and combinations thereof. In particular embodiments, the compositions of the present disclosure comprise sorbitol.

Suitable reactive oxygen scavengers for the compositions of the present disclosure include methionine. In particular embodiments, the compositions of the present disclosure comprise methionine.

Suitable surfactants for the compositions of the present disclosure include polysorbates (e.g., polysorbate 80), sodium dodecyl sulfate, dextran sulfate, and combinations thereof. In particular embodiments, the compositions of the present disclosure comprise polysorbate 80.

Suitable buffers for the compositions of the present disclosure include buffers, which provide a pH ranging from about 6 to about 8. In some embodiments, suitable buffers provide a pH ranging from about 6 to about 8 at a temperature of about 2-8° C. Specific buffers include histidine buffers, and phosphate buffers. In particular embodiments, the compositions of the present disclosure comprise histidine buffers.

The thermoreversible hydrogel composition of the described compositions includes a tri block copolymer having a general formulae ABA or BAB copolymer, wherein A is a hydrophilic block and B is a hydrophobic block. More specifically, A or B is selected from PEO ((Poly(ethylene oxide)), PLGA (poly(lactic-co-glycolic) acid, PLA (polylactic acid) and PPO (polypropylene oxide) PGA (Poly Glycolic Acid), PCL-(Polycaprolactonn), PCLA-Poly(ε-caprolactone-co-lactide), PCBCL-poly(α-carboxylate-co-α-benzylcarboxylate-ε-caprolactone), or includes at least two cyclic monomers selected from the group consisting of glycolide, lactide, e-caprolactone, p-dioxanone (1,4-dioxan-2-one), trimethylene carbonate (1,3-dioxan-2-one); 1,4-dioxepan-2-one (including its dimer 1,5,8,12-tetraoxacyclo-tetradecane-7,14-dione); 1,5-dioxepan-2-one; 6,6-dimethyl-1,4-dioxan-2-one; 2,5-diketomorpholine; pivalolactone; chidiethylpropiolactone; ethylene carbonate; ethylene oxalate; 3-methyl-1,4-dioxane-2,5 dione; 3,3-diethyl-1,4-dioxan-2, 5-dione, 6,8 dioxabicycloctane-7-one; beta-propiolactone; gama-butyrolactone, delta-valerolactone; epsilon-decalactone, 3-methyl-1,4-dioxane-2,5dione; 1,4-dioxane-2,5-dione; 2,5-diketomorpholine, alpha, alpha-diethylpropiolactone, gama-butyrolactone; 1,4-dioxepan-2-one, 1,5-dioxepan-2-one; 6,6-dimethyl-dioxepan-2-one; 6,6-dioxabicycloctane-7-one; or 5, 5-dimethyl-1,3-dioxan-2-one.

In other embodiments the thermoreversible hydrogel composition comprises at least one tri block copolymer having a general formula ABA or BAB copolymer, wherein A is a hydrophilic block and B is a hydrophobic block. In particular embodiments the tri block copolymer has an ABA formula of EPO/PPO/EPO block copolymer.

Suitable gelation temperature modifiers comprise polyethylene glycols (PEGs) such as PEG 200, PEG 300, PEG 400 and PEG-800. In particular embodiments, the compositions of the present disclosure comprise PEG-400.

In other embodiments of the present disclosure, the poloxamer comprises Poloxamer 407, Poloxamer 188, Poloxamer 124, Poloxamer 237, or Poloxamer 338 or a combination thereof, and has an average molecular weight of 8500-16000DA, inclusive.

In particular embodiments, the thermoreversible hydrogel of the present disclosure comprise 24-32% Poloxamer 407, 0.04-2% HPMC, and 0.5-2% PEG400 and water. In particular embodiments the hydrogels of the present disclosure comprise 31% Poloxamer 407, 0.05% HPMC, 1% PEG400 and water.

In particular embodiments, Poloxamer component in the pharmaceutical composition of the invention is present in concentrations of 20%-30% (w/w) of the pharmaceutical composition and any ranges therein, such as 22%-30%, 23%-28%, 24%-26%, In another particular embodiment, the Poloxamer is present in a concentration of 24.8% of the pharmaceutical composition In a particular embodiment, the thermoreversible hydrogel composition may further comprise at least one of a thickener agent, mucoadhesive enhancing agents, dissolution rate controlling agent, gelation temperature controlling agent, pH controlling agent, more of a thickener, a stabilizer, a reactive oxygen scavenger, a surfactant, a buffer, and a gelation temperature modifier. absorption enhancer/tight junction modifier/cell membrane permeability enhancer, organic acid or cyclodextrins.

In particular embodiments, dissolution rate controlling agents can include, but are not limited, to silicon dioxide or any derivatives thereof, nanoparticles or microparticles of Poly (Lactide-co-Glycolide (PLGA), polylactic acid (PLA), Polyglycolic acid (PGA), PLA-PEG or PLGA-PEG copolymers, nanoparticles or microparticles polystyrene or polymethyl methacrylate (PMMA), calcium carbonate, microcrystalline cellulose, aluminum hydroxide, Eudragit® NE, Eudragit® RS and RL, cellulose acetate and cellulose acetate butyrate, crospovidones, crosslinked sodium carboxymethylcellulose, crosslinked sodium carboxymethyl-starch, thickening agents, soy, iodinated aromatic compounds, cyclodextrin, and cholesterol.

In particular embodiments, gelation temperature controlling agents include, but are not limited to, urea, polyethylene glycol, short chain fatty acid and their salts (sodium octanoate, sodium dodecyl sulfate), ethanol, Glyceryl monostreatrate, Isopropyl myristate, and Polysorbate surfactants.

In particular embodiments, the pharmaceutical composition can be sterile.

In various embodiments, the compositions of the present invention comprise about 100 mg to about 900 mg zalifrelimab, including about 100 mg, about 150 mg, about 200 mg, about 250 mg, about 300 mg, about 350 mg, about 400 mg, about 450 mg, about 500 mg, about 550 mg, about 600 mg, about 650 mg or about 700 mg about 750 mg, about 800 mg, about 850 mg, or about 900 mg of zalifrelimab, including all ranges between any of these values.

In various embodiments, the concentrations of zalifrelimab in the pharmaceutical compositions of the present disclosure range from about 1 mg/mL to about 11 mg/mL, including about 1 mg/mL, about 1.3 mg/mL, about 2 mg/mL, about 2.7 mg/mL, about 3.3 mg/mL, about 4 mg/mL, about 4.7 mg/mL, about 5.3 mg/mL, about 6 mg/mL, about 6.7 mg/mL, about 7 mg/mL, about 7.9 mg/mL, about 8.6 mg/mL, about 9.3 mg/mL, about 10 mg/mL, about 10.5 mg/mL, or about 11 mg/mL, 50 mg/mL, or anywhere up to 60 mg/mL including all ranges between any of these values.

In particular embodiments, the compositions of the present disclosure comprise about 100 mg to about 750 mg of zalifrelimab, a poloxamer, a histidine buffer providing a pH in the range of about 6-8, hydroxypropyl methylcellulose, PEG-400, methionine, sorbitol, polysorbate 80, and water, thereby forming a thermoreversible hydrogel.

In particular embodiments, the present disclosure is directed to a pharmaceutical composition in the form of a thermoreversible hydrogel comprising poloxamer, water, and about 100 mg to about 750 mg zalifrelimab. Such compositions have a viscosity of not more than 1000 cP at 5° C., and a viscosity of $1\times10^6$ cP-$1.5\times10^7$ cP at 19° C.

In yet further particular embodiments, the pharmaceutical composition comprises Poloxamer, water, about 100 mg to about 750 mg zalifrelimab, a thickener, a stabilizer, a reactive oxygen scavenger, a surfactant, a buffer, solvent/co-solvent and optionally a gelation temperature modifier. In specific embodiments, the thickener is hydroxypropyl methylcellulose, the stabilizer is sorbitol, the reactive oxygen scavenger is methionine, the surfactant is polysorbate 80, the buffer is a histidine buffer.

Pharmaceutical Compositions and Methods of Treatment

Described herein are pharmaceutical compositions composed of a reverse thermal hydrogel combined with active agents that are antibodies such as a monoclonal antibodies, such as an immune checkpoint inhibitors for example but not limited to antibodies or fragments thereof that specifically bind to and inhibit the activity of CTLA-4, PDL-1 or PD-1. In other embodiments the active agents can be antibody drug conjugates (ADC), which are products in which a monoclonal antibody is linked to a small molecule drug with a stable linker, for example but not limited to Gemtuzumab-Ozogamicin. In particular embodiments the immune checkpoint inhibitor can be an inhibitor that is anti-PD1, anti-PDL1, anti-CTLA4, anti-KIR, anti-LAG3, anti-VISTA, anti-TIM3, anti-B7-H3, anti-B7-H4, and anti-BTLA. In particular embodiments, the immune checkpoint modulator is an antagonistic antibody for example: Pembrolizumab (Keytruda, MK-3475), Cemiplimab (AGEN-2034), Nivolumab (Opdivo, BMS-936558), Pidilizumab (CT-011), MEDI0680 (AMP514), TSR-042, AMP-224, Durvalumab (MEDI4736), Avelumab (MSB0010718C), Atezolizumab (MPDL3280A), CK-301, MDX1105 (BMS-936559), Ipilimumab (Yervoy), Tremelimumab (CP-675, 206), Lirlumab (BMS986015), IPH2101, Relatlimab (BMS986016), IMP321, TSR-033, JNJ-61610588, CA-170, BMS-986207, TSR022, Enoblituzumab (MGA271), MGD009, Zalifrelimab (AGEN-1884), AGEN-2041 (AGEN-1181), ADU-1604, AK 104, ALPN-202, BCD-145, BMS-986249, BPI-002, CBT-509, ADU-1604, ATOR 1144, ATOR-1015, and DS-5573a. The exemplary immune checkpoint inhibitor used herein is Zalifrelimab (AGEN-1884).

The described pharmaceutical compositions are used in methods for treating and as a composition for use in the treatment of cancer. In the specific embodiments the cancer is a urinary tract cancer, renal cancer, bladder cancer. The pharmaceutical composition of this instant invention can be administered either prior to or following standard tumor-removal surgery. In some embodiments, the described compositions inhibit tumor regrowth following surgery. In other embodiments, the described compositions decrease tumor size prior to surgery. In still other embodiments, the described compositions reduce or even eliminate the presence of tumors in the bladder.

In particular embodiments the described compositions include a reverse thermal hydrogel mixed with zalifrelimab solution. Such compositions are referred to herein as UGN-301.

Zalifrelimab is a recombinant, fully human immunoglobulin G1 monoclonal antibody that neutralizes the inhibitory effects of CTLA-4 on the immune responses of tumor-specific T cells. Zalifrelimab is intended to enhance tumor immune surveillance and anti-tumor immune responses by blocking CTLA-4 from binding to its ligands (cluster of differentiation [CD]80 and CD86), thereby neutralizing the negative regulatory effects of CTLA-4 on T cells.

Zalifrelimab was originally identified from a human donor-derived cellular antibody library, and an intravenous (IV) formulation is being developed as a monotherapy in patients with advanced or refractory cancer and as combination therapy with balstilimab (anti-PD1 antibody) in patients with metastatic or locally advanced solid tumors, including cervical cancer, inoperable or recurrent angiosarcoma, and metastatic, locally advanced, and/or unresectable squamous-cell carcinoma, adenosquamous carcinoma, or adenocarcinoma of the cervix.

In still other embodiments, the described methods provide the immune checkpoint inhibitor, and particularly zalifrelimab, mixed with a thermoreversible hydrogel in combination with an additional active chemotherapeutic or other anti-cancer agent, such as but not limited to mitomycin C (MMC), Imiquimod (UGN201) and gemcitabine or any pharmaceutical composition comprising one of mitomycin C (MMC), Imiquimod and gemcitabine.

As described further herein, the additional agent can be formulated with the checkpoint inhibitory agent, such as Zalifrelimab, in the thermoreversible hydrogel composition or can be formulated separately, such as in a solution formulation that is suitable for intravesical administration. Prior to combining with hydrogel, such agents can be provided in a variety of forms, including stable solutions, solid form, or lyophilized. In particular embodiments, the additional agent is imiquimod, referred to herein as UGN-201, or Gemcitabine or MMC. UGN-201 is a formulation of imiquimod, a toll-like receptor (TLR7) agonist, that has been optimized for intravesical administration into the bladder. This route of administration will allow for direct exposure to the target tissue and potentially provide an effective treatment for NMIBC while minimizing systemic exposure to imiquimod, or a small molecule chemotherapeutic agent such as but not limited to mitomycin or gemcitabine.

In other embodiments, the UGN-301 is provided as a combination treatment, with additional active ingredients such as UGN-201 (imiquimod), or chemotherapeutic agent such as but not limited to MMC or gemcitabine. The additional agent is administered at the same frequency as UGN-301, once weekly for 6-12 weeks. In particular embodiments, the additional agent is administered less frequently or more frequently than UGN-301, as determined by the skilled clinician.

In particular embodiments, the TLR-7 agonist, UGN-201, is administered at a concentration of 1 mg/ml-10 mg/ml [50 mg-500 mg], either prior to, subsequently to, or concurrently with the UGN-301 administration. In other embodiment UGN-201, is administered at dose of 200 mg [concentration of 4 mg/ml]. In some embodiments, 200 mg of UGN-201, at a concentration of 2-8 mg/mL. is administered.

There may be an optional wash between the administration of the UGN-201 and UGN-301. The wash may last 0-10 minutes, 10-20 minutes 20-30 minutes, 30-40 minutes, 40-50 minutes, 50-60 minutes, or up to 2-3 hours, or any time frame in between.

In additional embodiments, the UGN-201 may be left to dwell alone in the bladder, or bladder cavities for up to 1 hour, 2 hours. 3, hours, or any time in between.

As described herein, the pharmaceutical composition of the instant invention such as UGN301 designed for local administration into the bladder extends the release of zalifrelimab in the bladder, enhancing localized zalifrelimab concentrations, while avoiding significant systemic exposure which diminishes the systemic toxicity due to immune activation associated with CTLA-4 blockade.

The compositions of the present disclosure can be provided for use in treating a patient with urinary tract cancer and bladder cancer, including intermediate risk, low-grade, high-grade non-muscle-invasive bladder cancer including papillary (Ta), invades lamina propia (T1) and carcinoma in situ (CIS), muscle invasive bladder cancer (MIBC) and metastatic bladder cancer. For example, the disclosed pharmaceutical compositions can be formulated as thermoreversible hydrogel comprising about 100 mg to about 750 mg zalifrelimab, or alternatively can be provided as a kit comprising (a) an aqueous solution of 100 mg-750 mg of zalifrelimab, and (b) a thermoreversible hydrogel. In case of the kit, the aqueous solution (a) of zalifrelimab is mixed with the thermoreversible hydrogel (b) immediately up to 12 hours, 24 hours, 48 hours, 72 hour, 96 hours or up to 28 days prior to administration. This composition or kit is considered a monotherapy treatment, wherein the only active ingredient in the composition includes an anti-CTLA-4 antibody, such as zalifrelimab. The composition may be administered to the patient once weekly for a course of 6 weeks, followed by an optional maintenance period wherein the patient is administered at month 6 to month 12 of the initial dose up to an additional 6 doses of the composition.

In particular embodiments, the zalifrelimab solution comprises about 100 mg to about 750 mg of zalifrelimab, with a volume of about 15 mL, and the thermoreversible hydrogel (as described herein) has a volume of about 60 mL. In a specific example, after mixing the zalifrelimab solution and the thermoreversible hydrogel, the resulting therapeutic composition is about 75 mL of a hydrogel comprising about 100 mg to about 750 mg of zalifrelimab, however the volume of the combined solution comprising zalifrelimab with hydrogel composition can be varying from 30 ml to 150 ml.

The composition of the zalifrelimab solution can be any aqueous composition suitable to prevent loss of activity of the zalifrelimab for about 60 months when stored at about 2-8° C.

In particular embodiments, the zalifrelimab solution is stabilized for storage at 2-8° C. for up to 60 months by formulation of about 30-100 mg/mL zalifrelimab with 10-30 mM histidine, 200-300 mM sorbitol, 10-20 mM methionine, and 0.01-0.03% polysorbate 80, and is adjusted to a pH of 6-7 according to standard methods. In particular embodiments, the solution of zalifrelimab for combination with the poloxamer-based thermoreversible hydrogel includes 20 mM histidine, 250 mM sorbitol, 15 mM methionine, and 0.02% polysorbate 80. In such and additional embodiments, the hydrogel composition can include 25%-31% Poloxamer with a 100-700 mg of zalifrelimab used, PEG-1%, and HPMC-0.05%-2%. In optional embodiments, the same diluent as zalifrelimab (20 mM histidine, 250 mM sorbitol, 15 mM methionine, 0.02% polysorbate 80) is also used to dilute the thermoreversible hydrogel concentration.

In various other embodiments, the relative volumes of the zalifrelimab solution(s) and thermoreversible hydrogel may differ, provided that when mixed together, the amount of zalifrelimab in the resulting thermoreversible hydrogel ranges from about 100 mg to about 750 mg, the total volume of zalifrelimab-containing thermoreversible hydrogel ranges from about 50 mL to 100 mL, and the viscosity and gelation temperature characteristics of the compositions are consistent with those described herein. For example, but not limited to, the volume of the zalifrelimab solution(s) can range from about 10 mL to about 20 mL (including about 10 mL, about 15 mL, or about 20 mL, including ranges between any of these values), and the volume of the thermoreversible hydrogel can range from about 40 mL to about 100 mL (including about 40 mL, about 45 mL, about 50 mL, about 55 mL, about 60 mL, about 65 mL, or about 70 mL, about 80 mL, about 90 mL, or about 100 mL including ranges between any of these values).

The compositions of the present disclosure are administered intravesically to the bladder of a patient suffering from bladder cancer, for example a high-grade non-muscle-invasive bladder such as high-grade non-muscle-invasive bladder cancer including papillary (Ta), invades lamina propia (T1) and carcinoma in situ (CIS), muscle invasive bladder cancer (MIBC) and metastatic bladder cancer. Typical administration volumes range from about 50 mL to about 100 mL, depending on the volume required for a particular patient. In most embodiments, a single dose (e.g., about 50 ml, 60 mL, 70 mL, 75 or 80 mL of the thermoreversible hydrogel composition described herein containing about 100 mg to about 750 mg zalifrelimab) of the compositions described herein is administered intravesically, once weekly, for at least about 4 to 6 weeks. Thereafter, one or more doses of the disclosed pharmaceutical composition can be administered every 12 weeks. In another embodiment, intravesical administration of the described composition may be one time per week for up to 12 weeks, in particular, once weekly for up to 6 weeks, one time every 3 weeks for 12 weeks, one time every 2 weeks for 12 weeks, or 2 times per week for 6 weeks. Alternately, administration of the composition could be one time per month during months 6, 9, and 12 following the first administration, or may be up to 3 doses every 12 weeks for an extended period, or may be 3 additional doses over the duration of 6 to 12 months following the first administration or additional doses as determined by a skilled clinician.

In yet a further embodiment of the present disclosure, intravesical administration of the described composition is used to treat bladder cancer one time per week, up to 4 times, prior to a cystectomy.

In some embodiments, patients suffering from bladder cancer are treated with the zalifrelimab-containing compositions of the present invention in combination with a therapeutic amount of one or more additional active agents, as described herein, such as chemotherapeutic or a TLR agonist in use or development for treatment of bladder cancer. This treatment is considered a combination treatment that includes at least one additional active ingredient in addition to zalifrelimab, such as but not limited to, a TLR7 agonist such as imiquimod or a chemotherapeutic agent such as gemcitabine or mitomicin C. In some embodiments, the additional active agent, is administered prior to or after the zalifrelimab-containing composition. The additional active agent may be formulated in the same thermoreversible hydrogel containing zalifrelimab, such that the zalifrelimab and the additional active agent (e.g. imiquimod, mitomycin or gemcitabine) are administered together intravesically or in sequence to one another, with an optional wash between the components. Alternatively, the thermoreversible hydrogel containing zalifrelimab of the present disclosure and the additional active agent (e.g. imiquimod) are administered separately (both intravesically). When administered separately, the thermoreversible hydrogel containing zalifrelimab of the present disclosure can be administered either before the additional active agent or after the additional active agent (e.g. imiquimod, mitomycin or gemcitabine). The interval between administration of the thermoreversible hydrogel containing zalifrelimab and the additional active agent can be at least 1 hour to about 36 hours, 48 hours or 72 hours, with an optionally wash between administration of the zalifrelimab and the additional agent. In specific embodiments of the present disclosure mitomycin is administered at an amount of 20-200 mg. In yet further embodiment of the present disclosure, gemcitabine is administered in a gel formulation at an amount of 100-1000 mg; or in particular, 50-500 mg. In other embodiments, the gemcitabine is administered by instillation in a liquid formulation at amounts between 500-2000 mg.

When administered in combination with the thermoreversible hydrogel containing zalifrelimab of the present disclosure, the additional active agent (for example but not limited to imiquimod, mitomycin or gemcitabine) can be administered in any form of administration, preferably intravesically. As described herein the dosage regimens of the variously described combinations (e.g. zalifrelimab and an additional agent) and provision of the active agents vary by agent. In all regimens, zalifrelimab is provided in a reverse thermal gel as described. Additional agent(s) can be provided: prior with or without an intervening wash; with the antibody in the same reverse thermal gel formulation as the antibody; and/or after antibody treatment. In particular embodiments, the agent provided in addition the checkpoint inhibitor antibody is provided in an intravesical instillation solution. In other embodiments, the additional agent is provided in a reverse thermal gel solution to allow for extended sustained contact between the additional agent and the target area.

The compositions of the present disclosure are effective for treating cancers of the bladder, including low grade, and high-grade bladder cancers such as non-muscle invasive bladder cancer (NMIBC), particularly BCG-unresponsive NMIBC, and MIBC. Drugs such as zalifrelimab are effective immunotherapy agents, but when administered systemically, can have toxic side effects that limit both dose and schedule. The disclosed intravesically administered thermoreversible hydrogels avoid systemic administration of zalifrelimab, as the zalifrelimab is topically/locally applied to the target area, such as to the site of the bladder cancer. However, topically/locally applied drugs are not always therapeutically effective, as the drug must be released from the topical/local composition at a concentration and for a duration of contact, and must be able to diffuse through the patient's tissue so that a therapeutically effective dose is provided to the target site. Therapeutic antibodies, such as zalifrelimab, must also be sufficiently stable in the therapeutic formulation so as to retain a therapeutic level of activity. Accordingly, even though there are examples in the art of therapeutically effective, topically applied drug formulations, a person of skill in the art recognizes that the therapeutic effectiveness of topically/locally applied antibodies such as zalifrelimab is unpredictable. As described herein, intravesically administered thermoreversible hydrogels containing about 100 mg to about 750 mg of zalifrelimab, optionally in combination with at least one additional active agent are effective in treating bladder cancers as described herein.

The thermoreversible hydrogels of the present disclosure, when administered intravesically in a patient's bladder, are effective at providing and maintaining a therapeutically effective level of topical/local contact of zalifrelimab in the bladder for at least 4 hours after administration. In some embodiments, the local exposure of zalifrelimab after administration is maintained for about 4 to about 24 hours after administration, including about 4 hours, about 5 hours, about 6 hours, about 7 hours, about 8 hours, about 9 hours, about 10 hours, about 11 hours, or about 12 hours, including all ranges between any of these values.

In various embodiments after a single intravesical administration of about 70 mL of the thermoreversible hydrogel the present disclosure, containing 100 mg of zalifrelimab, the zalifrelimab pharmacokinetic area under the curve (AUC) ranges in urine is from about 907-1194 h*µg/mL.

In various embodiments, after a single intravesical administration of about 70 mL of the thermoreversible hydrogel the present disclosure, containing 300 mg of zalifrelimab, the zalifrelimab AUC ranges in urine from about 2330-7400 hr*ug/mL.

In various embodiments, after a single intravesical administration of about 70 mL of the thermoreversible hydrogel the present disclosure, containing 500 mg of zalifrelimab, the zalifrelimab AUC ranges in urine from about 3708-7758 hr*ug/mL.

In various embodiments, after a single intravesical administration of about 70 mL of the thermoreversible hydrogel the present disclosure, containing 700 mg of zalifrelimab, the zalifrelimab AUC ranges in the urine from about 4400-10000 hr*ug/mL.

In various embodiments after a single intravesical administration of about 70 mL of the thermoreversible hydrogel the present disclosure, containing 100 mg of zalifrelimab, the zalifrelimab Cmax ranges in urine is from about 130-272 µg/mL.

In various embodiments, after a single intravesical administration of about 70 mL of the thermoreversible hydrogel the present disclosure, containing 300 mg of zalifrelimab, the zalifrelimab Cmax ranges in urine from about 506-897 µg/mL.

In various embodiments, after a single intravesical administration of about 70 mL of the thermoreversible hydrogel the present disclosure, containing 500 mg of zalifrelimab, the zalifrelimab Cmax ranges in urine from about 628-1604 µg/mL.

In various embodiments, after a single intravesical administration of about 70 mL of the thermoreversible hydrogel the present disclosure, containing 700 mg of zalifrelimab, the zalifrelimab Cmax ranges in the urine from about 500-2000 µg/mL.

In various embodiments, after a single intravesical administration of about 70 mL of the thermoreversible hydrogel the present disclosure, containing 100 mg of zalifrelimab, the zalifrelimab AUC ranges in urine is from about 0.75-1.5 mg*hr/mL.

In various embodiments, after a single intravesical administration of about 70 mL of the thermoreversible hydrogel the present disclosure, containing 200 mg of zalifrelimab, the zalifrelimab AUC ranges in urine from about 1.5-3 mg*hr/mL.

In various embodiments, after a single intravesical administration of about 70 mL of the thermoreversible hydrogel the present disclosure, containing 300 mg of zalifrelimab, the zalifrelimab AUC ranges in urine from about 2.25-4.5 mg*hr/mL.

In various embodiments, after a single intravesical administration of about 70 mL of the thermoreversible hydrogel the present disclosure, containing 400 mg of zalifrelimab, the zalifrelimab AUC ranges in urine from about 3-6 mg*hr/mL.

In various embodiments, after a single intravesical administration of about 70 mL of the thermoreversible hydrogel the present disclosure, containing 500 mg of zalifrelimab, the zalifrelimab AUC ranges in urine from about 3.75-7.5 mg*hr/mL.

In various embodiments, after a single intravesical administration of about 70 mL of the thermoreversible hydrogel the present disclosure, containing 600 mg of zalifrelimab, the zalifrelimab AUC ranges in the urine from about 4.5-9 mg*hr/mL.

In various embodiments, after a single intravesical administration of about 70 mL of the thermoreversible hydrogel the present disclosure, containing 700 mg of zalifrelimab, the zalifrelimab AUC ranges in the urine from about 5.25-10.5 mg*hr/mL.

In various embodiments, after a single intravesical administration of about 70 mL of the thermoreversible hydrogel of the present disclosure, the zalifrelimab Cmax ranges in the urine from about 0.075-0.2 mg/mL, 0.15-0.4 mg/mL, 0.23-0.6 mg/mL, 0.3-0.8 mg/mL, 0.38-1.0 mg/mL, 0.45-1.2 mg/mL and 0.5-1.4 mg/mL.

In various embodiments, after a single intravesical administration of about 70 mL of the thermoreversible hydrogel the present disclosure, containing zalifrelimab, the zalifrelimab $t_{max}$ ranges in the urine from about 2-12 hours.

Anti-CTLA-4 antibodies have been shown to increase levels of immunomodulatory cytokines including but not limited to IL-2, IL-6 and IL-8. The locally (e.g., intravesically) administered zalifrelimab-containing compositions of the present disclosure also provide increased levels of immunomodulatory cytokines (e.g., levels one or more of IL-2, IL-4, IL-6, IL-8, IL-10, IFN-γ, and TNF-α) in bladder tissue, tumor tissue and in the urine after administration of at least one dose of the compositions according to the present disclosure. Levels of IL-2, 2-fold above untreated tissues correlate to therapeutically effective doses of the compositions of the present disclosure.

The locally (e.g., intravesically) administered zalifrelimab-containing compositions of the present disclosure increased expression of CD4$^+$ICOS$^{hi}$ T cells after administration of about 2 or more doses (once weekly) of the compositions of the present disclosure, relative to levels prior to administration of the zalifrelimab-containing compositions of the present disclosure. The increase in expression of CD4$^+$ICOS$^{hi}$ T cells ranges from about a twofold increase to more than about a ten-fold increase (including about a twofold, about a three-fold, about a four-fold, about a four-fold, about a five-fold, about a six-fold, about a seven-fold, about an eight-fold, about a nine-fold, about a ten-fold, or more than about a ten-fold increase in expression of CD4$^+$ICOS$^{hi}$ T cells.

The locally administered zalifrelimab-containing compositions of the present disclosure also increased the ratio of CD4$^+$ICOS$^{hi}$ T cells to CD4$^+$FOXP3$^+$ T cells after administration of about 2 or more doses (once weekly) of the compositions of the present disclosure, relative to the ratio prior to administration of the zalifrelimab-containing compositions of the present disclosure. Prior to administration, the CD4$^+$ICOS$^{hi}$/CD4$^+$FOX3P$^+$ ratio is generally less than 1; after administration of about 2 or more doses (once weekly) of the compositions of the present disclosure, the ratio increases by a factor of about 2 or more (including a factor of about 2× or more, about 3× or more, about 4× or more, or about 5× or more, including all ranges between any of these values).

Various systemically administered anti-CTLA-4 antibodies have been shown to induce immune related adverse events, including skin lesions (rash, pruritus, vitiligo), colitis, hypophysitis, thyroiditis, sarcoidosis, uveitis, Guillain-Barré syndrome, immune mediated cytopenia, and polymyalgia rheumatic/Horton (Anne Bertrand et al, BMC Medicine (2015)). When anti-CTLA-4 antibodies are administered systemically, the overall incidence of immune-related adverse events is quite high (over 70%), with a 24% incidence of high-grade immune related adverse events. In contrast, the intravesically administered zalifrelimab-containing compositions of the present disclosure exhibit a significantly lower incidence of immune-related adverse events, including a lower incidence of high-grade immune-related adverse events. For example, of the compositions of the present disclosure, when administered as described herein (e.g., intravesically, about once weekly for about 6-12 weeks) exhibit an overall incidence of adverse events of less than about 70% (including about 65%, about 60%, about 55%, about 50%, about 45%, about 40%, about 35%, about 30%, about 25%, about 20%, about 15%, or about 10%, including all ranges between any of these values), and an overall incidence of high-grade adverse events of less than about 20% (including about 20%, about 15%, about 10%, or about 5%, including all ranges between any of these values). Incidence evaluation is based on the number of immune related adverse events (irAEs) for global and specific irAEs (skin, gastrointestinal, endocrine, and hepatic diseases) and their grade (1-5; recorded according to Version 2, 3 or 4 of the Common Terminology Criteria for Adverse Events of the National Cancer Institute). Grades ≥3 are considered high-grade.

Systemically administered anti-CTLA-4 antibodies have been shown to increase levels of immunomodulatory cytokines such as IL-2, IL-4, IL-6, IL-8, IL-10, IFN-γ, and TNF-α. The topically/locally (e.g., intravesically) administered zalifrelimab-containing compositions of the present disclosure may also provide increased levels of immunomodulatory cytokines (e.g., levels one or more of IL-2, IL-4, IL-6, IL-8, IL-10, IFN-γ, and TNF-α) when exposed to up to 6 doses of the compositions of the present disclosure. Increased levels of cytokines correlate to the administration of the therapeutically effective doses of the compositions of the present disclosure.

The locally (e.g., intravesically) administered zalifrelimab-containing compositions of the present disclosure increased expression of CD4$^+$ICOS$^{hi}$ T cells after administration of about 3 or more doses (once weekly) of the compositions of the present disclosure, relative to levels prior to administration of the zalifrelimab-containing compositions of the present disclosure. The increase in expression of CD4$^+$ICOS$^{hi}$ T cells ranges from about a twofold increase to more than about a ten-fold increase (including about a twofold, about a three-fold, about a four-fold, about a four-fold, about a five-fold, about a six-fold, about a seven-fold, about an eight-fold, about a nine-fold, about a ten-fold, or more than about a ten-fold increase) in expression of CD4$^+$ICOS$^{hi}$ T cells.

The locally administered zalifrelimab-containing compositions of the present disclosure also increased the ratio of CD4$^+$ICOS$^{hi}$ T cells to CD4$^+$FOX3P$^+$ cells after administration of about 3 or more doses (once weekly) of the compositions of the present disclosure, relative to the ratio prior to administration of the zalifrelimab-containing compositions of the present disclosure. Prior to administration, the CD4$^+$ICOS$^{hi}$/CD4$^+$FOX3P$^+$ ratio is generally less than 1; after administration of about 3 or more doses (once weekly) of the compositions of the present disclosure, the ratio increases by a factor of about 2 or more (including a factor of about 2× or more, about 3× or more, about 4× or more, or about 5× or more, including all ranges between any of these values).

In order to detect changes in cytokines levels in urine and blood an immunoassay or proximity extension assay may be performed. Where an immunoassay utilizes antibodies directed against each cytokine together with a colorimetric reaction or electrochemiluminescence to detect and measure cytokines. Non-limiting examples of this technology include but are not limited to ELISAs or Mesoscale Discovery technology. Whereas a proximity extension assay (PEA) utilizes antibody-pairs directed against each cytokine and contain unique DNA sequences allowing hybridization only to antibody pairs. Subsequent proximity extension creates DNA reporter sequences which are amplified by real-time polymerase chain reaction. A non-limiting example of PEA is Olink.

Changes in immune cell populations and immune cell markers are detected by immunohistochemistry of tumor tissue or flow cytometry of immune cells in peripheral blood mononuclear cells (PBMCs) or urine. The concentration of zalifrelimab in human urine may be detected using an immunoassay together with a colorimetric reaction or electrochemiluminescence.

In certain embodiments, after intravesical administration at least about 80% of the zalifrelimab is released from the thermoreversible hydrogel within about 4 to about 24 hours.

In various embodiments, the thermoreversible hydrogel containing zalifrelimab is administered as a monotherapy to treat bladder cancers such as but not limited to low-grade or high-grade non-muscle-invasive bladder cancer, such as high-grade non-muscle-invasive bladder cancer including papillary (Ta), invades lamina propia (T1) and carcinoma in situ (CIS), muscle-invasive bladder cancer (MIBC) and metastatic bladder cancer.

In some embodiments, the thermoreversible hydrogel containing zalifrelimab is prepared by mixing a solution of zalifrelimab with a thermoreversible hydrogel as disclosed herein. In some embodiments, the solution of zalifrelimab and thermoreversible hydrogel is provided in the form of a kit containing separate vials of the solution of zalifrelimab and the thermoreversible hydrogel. In specific embodiments, the composition of zalifrelimab contains about 100 mg to about 750 mg zalifrelimab in the thermoreversible hydrogel. In a further specific embodiment, the volume of the composition administered to the patient is about 40-100 mL. In still further specific embodiment the volume of the composition administered to the patient is about 70 mL.

Additionally provided herein is a pharmaceutical composition, which includes a thermoreversible hydrogel comprising 20%-32% (w/w) of poloxamer and water; and about 100 to 900 mg zalifrelimab.

The described pharmaceutical contains a 0.67-10 mg/mL concentration of zalifrelimab, and has a viscosity of not more than 5000 cP at 5° C., and a viscosity of $1\times10^6$ cP-$9\times10^7$ cP at 19° C.

The described pharmaceutical contains a thermoreversible hydrogel with a gelation temperature of about 10° C. to about 18° C.

The described pharmaceutical contains a thermoreversible hydrogel with a gelation temperature of about 11° C. to about 17° C.

The described pharmaceutical contains a thermoreversible hydrogel with a gelation temperature of about 12° C. to about 16° C.

The described pharmaceutical composition contains a thermoreversible hydrogel with a gelation temperature of about 13° C. to about 15° C.

The described pharmaceutical composition contains a poloxamer 407.

The described pharmaceutical composition contains a thermoreversible hydrogel with at least a thickener, a stabilizer, a reactive oxygen scavenger, a surfactant, a buffer, and a gelation temperature modifier.

The described pharmaceutical composition has a thickener such as cellulose derivatives, a stabilizer such as sorbitol, a reactive oxygen scavenger such as methionine, a surfactant such as polysorbate 80, a buffer such as histidine buffer, and a gelation temperature modifier such as PEG-400.

The described pharmaceutical composition contains a thickener such as HPMC.

The described pharmaceutical composition comprises a thermoreversible hydrogel that is formulated for intravesical administration into a bladder, and wherein at least about 80% of the zalifrelimab is released from the thermoreversible hydrogel within about 4 to about 12 hours.

The described pharmaceutical composition further comprising at least one additional therapeutic/active agent.

The described pharmaceutical composition contains at least one additional therapeutic agent such as mitomycin C, imiquimod or gemcitabine.

The described pharmaceutical contains a concentration of mitomycin C of about 0.2 mg/mL to about 2 mg/mL.

The described pharmaceutical composition contains a concentration of gemcitabine of about 100-933 mg.

The described pharmaceutical composition has a pH of about 6 to about 8.

The described pharmaceutical composition produces after a single intravesical administration of about 70 mL, zalifrelimab urine concentrations exceeds 20 µg/mL.

The described pharmaceutical composition is substantially free from zalifrelimab aggregates after 24 hours, when stored at about 2° C.-8° C. for at least 24 hours.

The described pharmaceutical composition is for use in treatment of bladder cancer, wherein the thermoreversible hydrogel is administered intravesically into a bladder of a subject and remains in the bladder for at least 4 hours after administration thereby producing a voiding concentration of zalifrelimab of at least 20-70 µg/mL in urine of the subject.

The described pharmaceutical composition increases cytokine levels in the subject from between 2-24 hours subsequent to administration.

Described herein is a kit for preparing the pharmaceutical composition including: (a) about 40-80 mL of a thermoreversible hydrogel comprising poloxamer and water, and (b) about 10-20 mL of a solution comprising 50 mg-900 mg of zalifrelimab, wherein mixing (i) and (ii) forms about 50-100 mL of the pharmaceutical composition.

Further described herein are methods for treating a bladder cancer, comprising intravesically administering to a subject a pharmaceutical composition comprising: a thermoreversible hydrogel comprising 20%-32% (w/w) of poloxamer and water; and about 50 mg to about 900 mg zalifrelimab. to the bladder of a patient in need thereof, wherein the pharmaceutical composition substantially providing sustained release of zalifrelimab over a period of about 4 to about 24 hours.

The described method further comprises administering to the subject at least one additional therapeutic/active agent, such as imiquimod, mitomycin or gemcitabine or any mixture thereof.

The described method comprises zalifrelimab and at least one additional therapeutic/active agent that are formulated and administered together in the thermoreversible hydrogel.

The described comprises zalifrelimab and an additional therapeutic agent are administered separately.

The described method includes a pharmaceutical composition with an administered volume of about 50 mL to about 100 mL.

The described method includes a pharmaceutical composition that is administered to the patient at least 6 times at about one-week intervals.

The described method includes a pharmaceutical composition that is administered to the patient 6 times at one-week intervals.

The described method includes administering the pharmaceutical composition at least 6 times once weekly, then administering the pharmaceutical composition every 12 weeks.

The described method treat bladder cancer that is selected from high-grade or low grade NMIBC or MIBC.

Additionally described herein is a method for preparing the thermoreversible hydrogel which includes comprising mixing (a) a thermoreversible hydrogel comprising poloxamer and water, and (b) a solution comprising zalifrelimab.

The described method has a volumetric ratio of (a) to (b) of about 80 to about 20.

The described method includes a volume of the mixture of about 50 mL to about 100 mL.

Further described herein is a pharmaceutical composition in the form of a thermoreversible hydrogel, prepared by the described method.

Additionally described herein is method for treatment of a bladder cancer, which includes: intravesically administering to a subject a pharmaceutical composition comprising a thermoreversible hydrogel comprising poloxamer and water; and about 100 mg to about 900 mg zalifrelimab, wherein the concentration of zalifrelimab in the pharmaceutical composition is 0.67-10 mg/mL; wherein the thermoreversible hydrogel has a viscosity of not more than 1000 cP at 5° C., and a viscosity of $1 \times 10^6$ cP-$1.5 \times 10^7$ cP at 19° C., and wherein the hydrogel produces a voiding concentration of zalifrelimab of at least 20-70 μg/mL in urine of the subject, thereby treating the cancer.

Additional methods described herein are methods for the inhibiting re-growth of a bladder cancer, that include: intravesically administering to a subject a pharmaceutical composition comprising a thermoreversible hydrogel comprising poloxamer and water; and about 50 mg to about 900 mg zalifrelimab, wherein the concentration of zalifrelimab in the pharmaceutical composition is 2.85-10 mg/mL; wherein the thermoreversible hydrogel has a viscosity of not more than 1000 cP at 5° C., and a viscosity of $1 \times 10^6$ cP-$1.5 \times 10^7$ cP at 19° C., and wherein the hydrogel produces a voiding concentration of zalifrelimab of at least 20-70 μg/mL in urine of the subject, thereby inhibiting the regrowth of the cancer.

The described method includes a pharmaceutical composition that is administered once weekly for 3-9 weeks.

Further methods described herein is a method for reducing the size of a tumor prior to surgical removal of the tumor comprising: intravesically administering to a subject a pharmaceutical composition comprising a thermoreversible hydrogel comprising poloxamer and water; and about 100 mg to about 750 mg zalifrelimab, wherein the concentration of zalifrelimab in the pharmaceutical composition is 0.67-10 mg/mL; wherein the thermoreversible hydrogel has a viscosity of not more than 400 cP at 5° C., and a viscosity of $1 \times 10^6$ cP-$1.5 \times 10^7$ cP at 19° C., and wherein the hydrogel produces a voiding concentration of zalifrelimab of at least 20-70 μg/mL in urine of the subject, thereby diminishing the tumor prior to surgical removal of the tumor.

The described method includes a hydrogel which is administered once weekly for 1-4 weeks.

The described method further comprises intravesically administering to the subject an additional therapeutic agent selected from imiquimod, mitomycin C or gemcitabine.

The described method includes an additional therapeutic agent which is administered prior to, concurrently with, or following administration of the pharmaceutical composition.

The following examples are provided to illustrate certain particular features and/or embodiments. These examples should not be construed to limit the disclosure to the particular features or embodiments described.

EXAMPLES

The below Examples utilize the following components and adhere to the following parameters:

Zalifrelimab is formulated as an intravesical solution, referred to as UGN-301, a pharmaceutical composition containing the anti-CTLA4 antibody zalifrelimab (provided by Agenus Inc., Lexington MA), formulated for intravesical administration in a thermoreversible hydrogel, as described herein. Zalifrelimab is provided in amounts between 100-700 mg in a volume of about 70 mL. The resultant concentration range provided is 2.85-10 mg/mL. The resultant concentration of zalifrelimab in produced urine is at least 20-80 μg/mL for at least 6 hrs. UGN-301 is diluted prior to administration with the thermoreversible hydrogel and diluent to form a "UGN-301 admixture".

Imiquimod (UGN-201) is provided in a dosage of 200 mg in 50 mL (4 mg/mL) in a liquid formulation, is administered intravesically and held in the bladder for about 60 minutes.

Gemcitabine is provided at 1000 mg in a 50 mL (20 mg/mL) liquid formulation and is held in bladder for at least 90 minutes, followed by a saline wash (additional regimens and doses may be used, for example, doses up to 2000 mg, volume up to 100 mL, hold time up to 2 hours).

Dosage regimens are provided in an Induction Schedule: once weekly for up to 6-12 weeks, and followed by an Optional Maintenance Schedule which can be any of the following, as determined by the skilled clinician:
  once every 3 months (at 6, 9, and 12 months from initial treatment),
  3 weekly doses every 3 months (at 6, 9, and 12 months from initial treatment),
  2 weekly doses every 3 months (at 6, 9, and 12 months from initial treatment,
  once every 3 months (at 6, 9, and 12 months from initial treatment) then once every 6 months (at 18 and 24 months from initial treatment),
  3 weekly doses every 3 months (at 6, 9, and 12 months from initial treatment then 3 weekly doses every 6 months (at 18 and 24 months from initial treatment), or
  2 weekly doses every 3 months (at 6, 9, and 12 months from initial treatment then 2 weekly doses every 6 months (at 18 and 24 months from initial treatment).

AGEN1884 (Zalifrelimab) Drug Product Composition: including the amounts of all inactive ingredients, is as follows:

TABLE 1

Drug Product Composition

| Ingredient | Function | Grade | Quantity per mL | Concentration (%) |
|---|---|---|---|---|
| AGEN1884 | Active | N/A | 50 mg | 5 |
| L-Histidine Monohydrochloride | Buffer | USP, EP, JP | 1.16 mg | 0.116 |
| L-Histidine | Buffer | USP, EP, JP | 2.25 mg | 0.225 (20 mM) |
| Sorbitol | Stabilizing agent | USP, EP, JP | 45.5 mg | 4.55 (250 mM) |
| Methionine | Reactive oxygen species scavenger | USP, EP, JP | 2.2 mg | 0.22 (15 mM) |
| Polysorbate 80 | Surfactant | USP, EP, JP | 0.2 mg | 0.02 |
| Water for Injections | Solvent | USP, EP | QS to 1 mL | 89.87 |

AGEN1884 (Zalifrelimab) excipients' concentration in the final UGN-301 admixture. The concentration ranges between their content in the UGN-301 100 mg dose to the UGN-301 700 mg dose as listed in the table below:

TABLE 2

UGN-301 admixture

| | Concentration (w/w) | |
|---|---|---|
| Component | UGN-301 100 mg with 26% P407 | UGN-301 700 mg with 31% P407 |
| L-Histidine Monohydrochloride | 0.003 | 0.023 |
| L-Histidine | 0.006 | 0.045 |
| Sorbitol | 0.130 | 0.910 |
| Methionine | 0.006 | 0.044 |
| Polysorbate 80 | 0.001 | 0.004 |

AGEN1884 is very stable to aggregation. For all samples at all ambient temperatures analyzed (even at elevated temperatures) through the nine-month time point, no increase in aggregate was detected. Thus, it is seen herein that AGEN1884 (Zalifrelimab) is substantially free from zalifrelimab aggregates after 24 hours, when stored at about 2° C.-8° C. for at least 24 hours.

Hydrogel for UGN-301 Composition: The ingredients' content in the hydrogel is detailed below:

TABLE 3

Hydrogel for UGN-301 Composition

| UGN-301 Admixture Dose (mg) | % Poloxamer | % HPMC | % PEG |
|---|---|---|---|
| 700 | 31 | 0.05 | 1 |
| 500 | 29 | 0.047 | 0.933 |
| 300 | 27 | 0.044 | 0.875 |
| 100 | 26 | 0.041 | 0.824 |

Example 1—UGN-301 Treatment as a Monotherapy and Combination Therapy

Systemic anti-CTLA-4 therapy has demonstrated clinical efficacy against solid tumors, however, systemic CTLA-4 inhibition also has been associated with toxicity and adverse effects at systemically provided doses estimated to be in the range of 68-113 mg. Such effects are presumably due to aberrant systemic immune activation.

Described herein is the discovery that local administration of zalifrelimab into the bladder wall by intravesical administration in a thermoreversible hydrogel successfully increased drug concentrations in the target organ without significant systemic exposure, thereby diminishing the systemic toxicity and adverse effects associated with CTLA-4 blockade.

In total, twenty-seven recurrent NMIBC patients were treated intravesically with UGN-301 as a monotherapy or combination therapy as follows:

Monotherapy: a total of 20 patients were treated with UGN-301 alone as follows: 3 patients were treated with 100 mg UGN-301 (i.e., 100 mg zalifrelimab in the final UGN-301 formulation), 6 were treated with 300 mg UGN-301, 8 were treated with 500 mg UGN-301, and 3 were treated with 700 mg UGN-301.

During the Induction Period of the monotherapy, patients received 70 mL intravesical instillations of UGN-301 admixture as a reverse thermal hydrogel formulation once weekly for 6 weeks with a minimum of 4 days between treatments. Patients who were disease-free at week 12 and month 6 had the option to receive once-quarterly maintenance therapy of 70 mL intravesical UGN-301 admixture as a reverse thermal hydrogel formulation at 6, 9 and 12 months after the start of treatment.

Combination treatment with UGN-201: 3 patients were treated with 300 mg UGN-301 and 200 mg UGN-201; 1 patient was treated with 500 mg UGN-301 and 200 mg UGN-201 in combination.

During the Induction Period of UGN-301+UGN-201, patients received intravesical instillations of 200 mg/50 mL (4 mg/mL) UGN-201 as a liquid formulation, held in the bladder for 1 hour and drained, followed by intravesical instillations of 70 mL UGN-301 as a reverse thermal hydrogel formulation once weekly for 6 weeks with a minimum of 4 days between treatments. Patients who were disease-free at week 12 and month 6 had the option to receive once quarterly maintenance therapy of 200 mg/50 mL (4 mg/mL) UGN-201 as a liquid formulation, held in the bladder for 1 hour and drained, followed by 70 mL intravesical UGN-301 admixture as a reverse thermal hydrogel formulation at 6, 9 and 12 months after the start of treatment.

Combination treatment with gemcitabine: 3 patients were treated with 300 mg UGN-301 and 1000 mg gemcitabine in combination. During the Induction Period, patients received intravesical instillations of 1000 mg/50 mL (20 mg/mL) gemcitabine as a liquid formulation, held in the bladder for 90 minutes and drained, followed by intravesical instillations of 70 mL UGN-301 as a reverse thermal hydrogel formulation once weekly for 6 weeks with a minimum of 4 days between treatments. Patients who were disease-free at week 12 and month 6 had the option to receive once quarterly maintenance therapy of 1000 mg/50 mL (20 mg/mL) gemcitabine as a liquid formulation, held in the bladder for 90 minutes and drained, followed by 70 mL intravesical UGN-301 admixture as a reverse thermal hydrogel formulation at 6, 9 and 12 months after the start of treatment. During each instillation, the bladder was washed with saline after gemcitabine was drained to increase the pH in the bladder prior to instilling UGN-301.

At all dose levels evaluated, treatment emergent adverse events (TEAE) were mild or moderate in severity except for 2 severe events of a urinary tract infection which were not considered related to study treatment or procedure (Table 4). No patient had a serious TEAE or a TEAE leading to treatment discontinuation. Additionally, no dose limiting toxicities and no immune-related adverse events (irAEs) were observed.

TEAEs reported for >1 patient receiving UGN-301 as a monotherapy were haematuria, UTI, nausea, dysuria and urinary retention in 2 patients each (Table 5). TEAEs reported for >1 patient were urinary incontinence with UGN-301 and UGN-201 and dysuria with UGN-301+ gemcitabine (Table 5).

TABLE 4

Overall Summary of TEAEs

| Category | Arm A (UGN-301 Monotherapy) | | | | Arm B (UGN-301 300 mg + UGN-201 200 mg) | Arm B (UGN-301 500 mg + UGN-201 200 mg) | Arm C (UGN-301 300 mg + Gemcitabine 1000 mg) |
|---|---|---|---|---|---|---|---|
| | 100 mg N = 3 n (%) | 300 mg N = 6 n (%) | 500 mg N = 8 n (%) | 700 mg N = 3 n (%) | N = 3 n (%) | N = 1 n (%) | N = 3 n (%) |
| Any TEAE | 2 (66.7) | 6 (100) | 4 (50) | 1 (33.3) | 3 (100) | 1 (100.0) | 2 (66.7) |
| TEAEs by maximum severity | | | | | | | |
| Mild | 2 (66.7) | 3 (50.0) | 2 (25.0) | 0 | 0 | 1 (100.0) | 2 (66.7) |
| Moderate | 0 | 3 (50.0) | 1 (12.5) | 1 (33.3) | 2 (66.7) | 0 | 0 |
| Severe or medically significant | 0 | 0 | 1 (12.5) | — | 1 (33.3) | 0 | 0 |
| Life-threatening | 0 | 0 | 0 | — | 0 | 0 | 0 |
| Death | 0 | 0 | 0 | — | 0 | 0 | 0 |
| Any treatment or procedure related TEAE | 1 (33.3) | 3 (50.0) | 3 (37.5) | 1 (33.3) | 3 (100.0) | 1 (100.0) | 2 (66.7) |
| Any UGN-301 related TEAE | 1 (33.3) | 1 (16.7) | 2 (25.0) | 0 | 1 (33.3) [a] | 1 (100.0) | 2 (66.7) [a] |
| Any UGN-201 related TEAE | N/A | N/A | N/A | N/A | 1 (33.3) [a] | 0 | N/A |
| Any gemcitabine related TEAE | N/A | N/A | N/A | N/A | N/A | N/A | 2 (66.7) |
| Any procedure related TEAE | 1 (33.3) | 2 (33.3) | 1 (12.5) | 1 (33.3) | 3 (100.0) | 0 | 0 |
| Any TEAE leading to treatment discontinuation | 0 | 0 | 0 | 0 | 0 | 0 | 0 |
| Any serious TEAE | 0 | 0 | 1 (12.5) | 0 | 1 (33.3) | 0 | 0 |
| Any treatment or procedure related serious TEAE | 0 | 0 | 1 (12.5) | 0 | 0 | 0 | 0 |
| Any treatment related serious TEAE | 0 | 0 | 0 | 0 | 0 | 0 | 0 |
| Any procedure related serious TEAE | 0 | 0 | 1 (12.5) | 0 | 0 | 0 | 0 |

N = number of patients in each treatment group; n = number of patients with event; TEAE = treatment-emergent adverse event.
[a] Treatment related TEAEs in the combination arms were attributed to both treatments.
Note:
Percentages are based on the number of patients in each treatment group.

TABLE 5

Summary of TEAEs by Preferred Term

| TEAE Preferred Term | Arm A (UGN-301 Monotherapy) | | | | Arm B (UGN-301 300 mg + UGN-201 200 mg) | Arm B (UGN-301 500 mg + UGN-201 200 mg) | Arm C (UGN-301 300 mg + Gemcitabine 1000mg) |
|---|---|---|---|---|---|---|---|
| | 100 mg N = 3 n (%) | 300 mg N = 6 n (%) | 500 mg N = 8 n (%) | 700 mg N = 3 n (%) | N = 3 n (%) | N = 1 n (%) | N = 3 n (%) |
| Patients with any TEAE | 2 (66.7) | 6 (100.0) | 4 (50.0) | 1 (33.3) | 3 (100.0) | 1 (100.0) | 2 (66.7) |
| Asthenia | 0 | 0 | 1 (12.5) | 0 | 0 | 0 | 0 |
| Dysuria | 1 (33.3) | 0 | 1 (12.5) | 0 | 1 (33.3) | 0 | 2 (66.7) |
| Haematuria | 0 | 1 (16.7) | 1 (12.5) | 0 | 1 (33.3) | 0 | 0 |
| Nausea | 0 | 2 (33.3) | 0 | 0 | 0 | 0 | 0 |
| Urinary tract infection | 0 | 1 (16.7) | 1 (12.5) | 1 (33.3) | 1 (33.3) | 0 | 0 |

TABLE 5-continued

| | Summary of TEAEs by Preferred Term | | | | | | |
|---|---|---|---|---|---|---|---|
| | Arm A (UGN-301 Monotherapy) | | | | Arm B (UGN-301 300 mg + UGN-201 200 mg) | Arm B (UGN-301 500 mg + UGN-201 200 mg) | Arm C (UGN-301 300 mg + Gemcitabine 1000mg) |
| TEAE Preferred Term | 100 mg N = 3 n (%) | 300 mg N = 6 n (%) | 500 mg N = 8 n (%) | 700 mg N = 3 n (%) | N = 3 n (%) | N = 1 n (%) | N = 3 n (%) |
| Urinary incontinence | 0 | 0 | 0 | 0 | 2 (66.7) | 0 | 0 |
| Urinary retention | 0 | 2 (33.3) | 0 | 0 | 1 (33.3) | 0 | 0 |
| Back pain | 0 | 1 (16.7) | 0 | 0 | 0 | 0 | 0 |
| Cataract | 0 | 1 (16.7) | 0 | 0 | 0 | 0 | 0 |
| Culture urine positive | 0 | 1 (16.7) | 0 | 0 | 0 | 0 | 0 |
| Dental caries | 1 (33.3) | 0 | 0 | 0 | 0 | 0 | 0 |
| Headache | 0 | 1 (16.7) | 0 | 0 | 0 | 0 | 0 |
| Fatigue | 0 | 0 | 0 | 0 | 0 | 1 (100.0) | 0 |
| Flatulence | 0 | 0 | 0 | 0 | 0 | 0 | 1 (33.3) |
| Uncoded | 0 | 1 (16.7) | 0 | 0 | 0 | 0 | 0 |

N = number of patients in each treatment group; n = number of patients with event; TEAE = treatment-emergent adverse event.
<sup>a</sup> One patient had a serious TEAE of urinary tract infection considered by the investigator to be severe or medically significant and related to study procedure.
Note:
Percentages are based on the number of patients in each treatment group.

Results

In addition to not causing serious side effects UGN-301 treatment was also effective at treating the target bladder cancer at doses of 300 mg UGN-301 and above. Half of the patients dosed with 300 mg UGN-301 were disease-free 9 months or more and 2/5 patients dosed with 500 mg UGN-301 were disease-free 3-month or more after the start of therapy.

Furthermore, it was observed that patients treated intravesically with 200 mg UGN-201 and 300 mg UGN-301 in combination is also efficacious since all 3 patients receiving the combination were disease free 3 months after commencement of the therapy.

In addition, it was observed that patients treated intravesically with 1000 mg UGN-201 and 300 mg UGN-301 in combination is efficacious. As shown herein, two patients were disease free 3 months after commencement of the therapy.

These above-noted results are summarized in Table 6.

Conclusion

As seen above, the monotherapy treatment of NMIBC with UGN-301 as a monotherapy, in combination with UGN-201, or in combination with a chemotherapeutic agent, resulted in a safe and effective treatment course. Thus, local administration of zalifrelimab into the bladder by intravesical administration in a thermoreversible hydrogel (UGN-301) allows for an increased drug concentration in the target organ without significant systemic exposure, thereby diminishing systemic toxicity and adverse effects associated with CTLA-4 blockade, which proves advantageous over systemic administration for the treatment of NMIBC.

Example 2—Pharmacokinetics of UGN-301 Treatment

Serum was collected at weeks 1-6 prior to dosing and at 1, 2, 6, and 12 h (±15 min) and 24 h (±1 h) after UGN-301 administration at weeks 1 and 6 to determine the concen-

TABLE 6

| Summary of Therapy Efficacy- Monotherapy and Combination | | | | |
|---|---|---|---|---|
| | 3 Months | 6 Months | 9 Months | 12 Months |
| ArmA Dose Level | | | | |
| 100 mg (N = 3) | 1/3 Recurrence free | 1/3 Recurrence free | 0/3 Recurrence free | |
| 300 mg (N = 6) | 3/6 Recurrence free | 3/6 Recurrence free | 3/6 Recurrence free | 2/5 Recurrence free |
| 500 mg (N = 5) | 2/5 Recurrence free | 1/4 Recurrence free | | |
| Arm B Dose Level | | | | |
| 300 mg (N = 3) | 3/3 Recurrence free | | | |
| Arm C Dose Level | | | | |
| 300 mg (N = 3) | 2/2 Recurrence Free | | | | tration of zalifrelimab in circulation. The samples collected from 16 patients (14 patients receiving 100-500 mg UGN-301 alone, 2 patients receiving 300 mg UGN-301 and 200 mg UGN-201 in combination) did not show systemic exposure to zalifrelimab following single and repeat dosing of UGN-301 administered intravesically once weekly for up to 6 weeks. The sustained concentration of zalifrelimab detected in urine overtime was below the level of quantitation indicating that there was no exposure. This data indicates that intravesical administration of zalifrelimab is likely to have reduced systemic adverse events.

Anti-zalifrelimab antibody data from 7 patients receiving doses of UGN-301 from 100-500 mg indicate that antibodies against zalifrelimab were not produced and thus did not influence zalifrelimab systemic exposure.

Analysis of urine concentrations from patients administered 100, 300 or 500 mg UGN-301 once weekly was performed (Table 7). The maximum urine concentration occurred 2 hours after administration of UGN-301 at all dose levels and was 197+/−77, 627+/−174, and 1106+/−314 µg/mL when 100, 300 and 500 mg UGN-301 was administered, respectively. Zalifrelimab was detected in urine for at least 12 hours at all dose levels evaluated and detected up to 22-24 hours after administration of 300 and 500 mg UGN-301 in some patients. These data demonstrate that the maximum urine concentration and AUC increase in an approximately dose proportional manner from 100 to 500 mg. Utilizing these available data, the time above threshold concentration (70 g/mL), where maximal inhibition of CTLA-4 ranges from 4.7-14.7 hours. (FIG. 1 and Table 7).

TABLE 7

Analysis of urine concentrations

| UGN-301 Dose (mg) | AUC Range (h*ug/mL) | Cmax Range (ug/mL) | $T_{threshold}$ (hr) |
|---|---|---|---|
| 100 | 907-1194 | 6-389 | 4.7-8.1 |
| 300 | 2330-7400 | 506-897 | 7.9-14.7 |
| 500 | 3708-7758 | 628-1604 | 6-12 |

This example demonstrates that local administration of UGN-301 successfully produces a sustained release of Zalifrelimab, which can be detected in the patients' urine up to 24 hours post-administration.

Example 3—Changes in Cytokine Expression Resultant of UGN-301 Treatment

The Olink proximity extension assay (PEA) technology was utilized to evaluate changes in 92 proteins, including many cytokines, in urine following intravesical administration of 100 mg or 300 mg UGN-301. Overall, maximal changes occur within the first 12 hrs and most proteins returned or were returning to baseline by 24 hours. Treatment with UGN-301 resulted in changes in abundance for 89/92 proteins at any time or dose. Evaluation of proteins that increased most consistently across patients and dose revealed that cytokines HO-1, CASP-8, CCL20, and ARG1 increased ≥2 log 2 fold between 2-24 hours following treatment with 100 or 300 mg UGN-301. The cytokines GAL-9, TRAIL, ADGRG1, IFN-γ and CXCL9 increased ≥2 log 2 fold between 2-24 hrs following treatment with 300 mg UGN-301. The cytokines CCL3, CCL4, GZMA and IL18 increased ≥2 log 2 fold between 2-24 hours following treatment with 100 mg UGN-301. Together, these data indicate that local administration of UGN-301 leads to rapid increases in immunomodulatory cytokines.

Example 4—Monotherapy-Prevention of Recurrence

A subject, such as described in Example 1, but who has undergone bladder resection surgery to remove tumors, is administered an intravesical regimen of an initial dose of 100 mg UGN-301, possibly escalating until 700 mg UGN-301 to reach and maintain a concentration of zalifrelimab in the urine of 20-80 µg/mL for at least 6 hours. UGN-301 is administered weekly for at least 6 weeks. This is seen to prevent the regrowth of the tumor after surgical removal.

The subject will optionally be treated during a maintenance period in which the patient will receive up to 3 additional doses of their assigned treatment once every 3 months (at 6, 9, and 12 months after the start of treatment).

Example 5—Monotherapy-Neoadjuvant Treatment

A subject, such as described in Example 1, but prior to undergoing bladder resection surgery is administered an intravesical regimen of an initial dose of 100 mg antibody in UGN-301, possibly escalating until 700 mg antibody in UGN-301, to maintain a concentration of zalifrelimab in the urine of 20-80 g/mL for at least 6 hours. UGN-301 is administered weekly for 1-4 weeks prior to surgery, and it is seen that this treatment diminishes tumor size prior to surgery.

The subject will optionally be treated during a maintenance period in which the patient will receive up to 3 additional doses of their assigned treatment once every 3 months (at 6, 9, and 12 months after the start of treatment).

Example 6—Combination Therapy (UGN-301+UGN-201)—Prevention of Recurrence

This example is similar to Example 1 except instead of the UGN-301 monotherapy, the subject is administered a combination of zalifrelimab and imiquimod. A subject in need is administered a weekly combination regimen administered intravesically for at least 6 weeks where 200 mg/50 mL (4 mg/mL) UGN-201, as a liquid formulation, is held in the bladder for 1 hour and drained/washed, followed by 100-700 mg UGN-301 (zalifrelimab) formulated in a thermoreversible hydrogel to maintain a concentration of zalifrelimab in the urine of 20-80 µg/mL for at least 6 hours. It is seen that this prevents the regrowth of the tumor after surgical removal of tumors.

Example 7—Combination Therapy (UGN-301+UGN-201)—Neoadjuvant Treatment

This example is similar to Example 1, except instead of the UGN-301 monotherapy, the subject is administered a combination of zalifrelimab and imiquimod. A subject in need is administered a weekly combination regimen intravesically for 1-4 weeks where 200 mg/50 mL (4 mg/mL) UGN-201, as a liquid formulation, is held in the bladder for 1 hour and drained, followed by 100-700 mg UGN-301 (zalifrelimab) formulated in a thermoreversible hydrogel to maintain a concentration of zalifrelimab in the urine of 20-80 µg/mL for at least 6 hours. It is seen that this treatment diminishes tumor size prior to surgical removal of the tumor(s) or bladder.

Example 8—Combination Therapy (UGN-301+Gemcitabine)—Complete Response

This example is similar to Example 1, except instead of the UGN-301 monotherapy, the subject is administered a combination of zalifrelimab and gemcitabine. A subject in need is administered a weekly combination regimen intravesically for at least 6 weeks where 1000 mg/50 mL (20 mg/mL) gemcitabine is held in the bladder for 90 minutes and drained, followed by a saline wash and followed with an initial dose of 100 mg UGN-301, possibly escalating until 700 mg UGN-301 formulated in a thermoreversible hydrogel to maintain a concentration of zalifrelimab in the urine of 20-80 µg/mL for at least 6 hours. It is seen that this treatment leads to the disappearance of all detectable tumor lesions using established techniques in the field.

Example 9—Combination Therapy (UGN-301+Gemcitabine)—Prevention of Recurrence This example is similar to Example 1, except instead of the UGN-301 monotherapy, the subject is administered a combination of zalifrelimab and gemcitabine. A subject in need is administered a weekly combination regimen intravesically for at least 6 weeks where 1000 mg/50 mL (20 mg/mL) gemcitabine is held in the bladder for 90 minutes and drained, followed by a saline wash and followed with an initial dose of 100 mg UGN-301, possibly escalating until 700 mg UGN-301 formulated in a thermoreversible hydrogel to maintain a concentration of zalifrelimab in the urine of 20-80 µg/mL for at least 6 hours. It is seen that this treatment prevents the regrowth of the tumors after surgical removal of tumors.

Example 10—Combination Therapy (UGN-301+Gemcitabine)—Neoadjuvant Treatment

This example is similar to Example 1, except instead of the UGN-301 monotherapy, the subject is administered a combination of zalifrelimab and gemcitabine. A subject in need is administered a weekly combination regimen intravesically for 1-4 weeks where 1000 mg/50 mL (20 mg/mL) gemcitabine is held in the bladder for 90 minutes and drained, followed by a saline wash then followed with an initial dose of 100 mg UGN-301, possibly escalating until 700 mg UGN-301 formulated in a thermoreversible hydrogel to maintain a concentration of zalifrelimab in the urine of 20-80 µg/mL for at least 6 hours. It is seen that this treatment diminishes tumor size prior to surgical removal of the tumor(s) or bladder.

Example 11—Combination Therapy (UGN-301+Mitomycin C) Complete Response

This example is similar to Example 1, except instead of the UGN-301 monotherapy, the subject is administered a combination of zalifrelimab and mitomycin C. A subject in need is administered a weekly combination regimen intravesically for 6 weeks where 75 mg mitomycin C and 200-700 mg UGN-301 (zalifrelimab), formulated together in a thermoreversible hydrogel, to maintain a concentration of zalifrelimab in the urine of 20-80 µg/mL for at least 6 hours leads. This treatment is seen to lead to the disappearance of all detectable tumor lesions using established techniques in the field.

Example 12—Combination Therapy (UGN-301+Mitomycin C)—Prevention of Recurrence This example is similar to Example 1, except instead of the UGN-301 monotherapy, the subject is administered a combination of zalifrelimab and mitomycin C. A subject in need is administered a weekly combination regimen intravesically for 6 weeks where 75 mg mitomycin C and 200-700 mg UGN-301 (zalifrelimab), formulated together in a thermoreversible hydrogel, to maintain a concentration of zalifrelimab in the urine of 20-80 µg/mL for at least 6 hours. It is seen that this treatment prevents the regrowth of the tumor after surgical removal of tumors.

Example 13—Combination Therapy (UGN-301+Mitomycin C)—Neoadjuvant Treatment

This example is similar to Example 1, except instead of the UGN-301 monotherapy, the subject is administered a combination of zalifrelimab and mitomycin C. A subject in need is administered a weekly combination regimen intravesically for 1-4 weeks where 75 mg mitomycin C and 200-700 mg UGN-301 (zalifrelimab), formulated together in a thermoreversible hydrogel, to maintain a concentration of zalifrelimab in the urine of 20-80 µg/mL for at least 6 hours. This treatment is seen to diminish tumor size prior to surgical removal of the tumor(s) or bladder.

The invention claimed is:

1. A method for treating a urinary tract cancer, comprising:
   locally administering to a subject in need thereof a pharmaceutical composition formulated to provide sustained release of zalifrelimab over a period of about 2 to about 24 hours, wherein the pharmaceutical composition comprises an admixture of:
   i. a thermoreversible hydrogel comprising 20%-32% (w/w) of poloxamer and water; and
   ii. a solution comprising about 100 mg to about 700 mg zalifrelimab, thereby producing a detectable zalifrelimab urine void concentration of at least 20 µg/mL after at least 2 hours of administration,
   thereby treating the urinary tract cancer.

2. The method of claim 1, wherein the thermoreversible hydrogel and solution comprising zalifrelimab are mixed prior to administration of the composition.

3. The method of claim 1, further comprising administering to the subject at least one additional therapeutic agent.

4. The method of claim 3, wherein the at least one additional therapeutic agent comprising imiquimod, mitomycin C, gemcitabine or any combination thereof.

5. The method of claim 4, wherein the zalifrelimab and the additional therapeutic agent are administered separately, with an optional wash between the administration of the two agents.

6. The method of claim 1, wherein the pharmaceutical composition is administered to the patient at least 6 times at about one-week intervals.

7. The method of claim 6, further comprising administering the pharmaceutical composition at least once quarterly from month 6 from the first administration until month 12 from the first administration of the pharmaceutical composition.

8. The method of claim 1, wherein the urinary tract cancer is a bladder cancer, and the bladder cancer is high-grade or low grade NMIBC, MIBC, or carcinoma in situ (CIS).

9. The method of claim 1, wherein the composition is administered prior to surgical removal of a tumor or after removal of a tumor.

10. A method for treatment of a bladder cancer or regrowth of bladder cancer, comprising:
    intravesically administering to a subject a pharmaceutical composition comprising an admixture of:
    i. a thermoreversible hydrogel comprising poloxamer and water; and
    ii. a solution comprising about 100 mg to about 700 mg zalifrelimab,
    wherein the concentration of zalifrelimab in the pharmaceutical composition is 0.67-10 mg/mL;
    wherein the thermoreversible hydrogel has a viscosity of not more than 5000 cP at 5° C., and a viscosity of $1 \times 10^6$ cP-$9 \times 10^7$ cP at 17° C., and
    wherein the hydrogel produces a voiding concentration of detectable zalifrelimab of at least 20-70 µg/mL in urine of the subject after at least 2 hours of administration, thereby treating the cancer.

11. The method of claim 10, further comprising intravesically administering to the subject an additional therapeutic agent selected from imiquimod, mitomycin C or gemcitabine.

12. The method of claim 10, wherein the pharmaceutical composition is administered once weekly for 3-9 weeks.

13. The method of claim 11, wherein the additional therapeutic agent is administered prior to, concurrently with, or following administration of the pharmaceutical composition.

14. A pharmaceutical composition, comprising:
    i. a thermoreversible hydrogel comprising 20%-32% (w/w) of poloxamer and water; and
    ii. about 30-100 mg/mL zalifrelimab formulated in a solution comprising 10-30 mM histidine, 200-300 mM sorbitol, 10-20 mM methionine, and 0.01-0.03% polysorbate 80, and is adjusted to a pH of 6-7.

15. The pharmaceutical composition of claim 14, wherein the thermoreversible hydrogel comprises 25%-32% (w/w) poloxamer, and the zalifrelimab solution comprises about 50 mg/mL zalifrelimab, 20 mM histidine, 250 mM sorbitol, 15 mM methionine, and 0.02% polysorbate 80.

16. The pharmaceutical composition of claim 15, wherein the zalifrelimab in the pharmaceutical composition is present at a concentration of 0.67-10 mg/mL; and wherein the said pharmaceutical composition has a viscosity of not more than 5000 cP at 5° C., and a viscosity of $1 \times 10^6$ cP-$9 \times 10^7$ cP at 17° C.

17. A method for treatment of a bladder cancer comprising:
    (a) preparing a composition with an effective amount of a zalifrelimab solution into a thermoreversible hydrogel; and
    (b) administering the composition to the bladder
    wherein the thermoreversible hydrogel comprises: (i) 20% to 32% (w/w) poloxamer 407; (ii) 0.02% to 0.5% (w/w) hydroxypropylmethylcellulose; (iii) 0.5% to 1% (w/w) PEG-400; and (iv) water.

18. The method of claim 17, wherein the composition comprises 24.8% poloxamer.

19. The method of claim 17, wherein the zalifrelimab has a concentration of 0.67-10 mg/mL.

20. The method of claim 17, further comprising intravesically administering to the subject an additional therapeutic agent selected from imiquimod, mitomycin C or gemcitabine.

21. The method of claim 1, wherein the local administration of the pharmaceutical composition minimizes systemic exposure and toxicity of zalifrelimab in the subject.

* * * * *